US007359803B2

(12) United States Patent
Gysling et al.

(10) Patent No.: US 7,359,803 B2
(45) Date of Patent: Apr. 15, 2008

(54) APPARATUS AND METHOD FOR MEASURING PARAMETERS OF A MIXTURE HAVING SOLID PARTICLES SUSPENDED IN A FLUID FLOWING IN A PIPE

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 10/349,716

(22) Filed: Jan. 23, 2003

(65) Prior Publication Data

US 2003/0154036 A1    Aug. 14, 2003

Related U.S. Application Data

(60) Provisional application No. 60/426,724, filed on Nov. 15, 2002, provisional application No. 60/425,436, filed on Nov. 12, 2002, provisional application No. 60/375,847, filed on Apr. 24, 2002, provisional application No. 60/359,785, filed on Feb. 26, 2002, provisional application No. 60/351,232, filed on Jan. 23, 2002.

(51) Int. Cl.
*G01N 31/00* (2006.01)
(52) U.S. Cl. ........................................... 702/25
(58) Field of Classification Search ............ 702/23–25, 702/32, 35, 39, 45, 47, 48, 50, 76, 96, 98, 702/103–106, 136–138, 141, 142, 191, 195, 702/75; 73/861.02, 861.22, 861.23, 861.355, 73/861.356, 861.357, 862.581, 862.61, 592
See application file for complete search history.

(56) References Cited

U.S. PATENT DOCUMENTS 3,751,979 A * 8/1973 Ims ........................ 73/861.27
3,781,895 A   12/1973 Monser .................... 343/708
3,851,521 A   12/1974 Ottenstein ............... 73/40.5 R
3,885,432 A * 5/1975 Herzl ...................... 73/861.22

(Continued)

FOREIGN PATENT DOCUMENTS

DE    4306119    9/1994

(Continued)

OTHER PUBLICATIONS

"Noise and Vibration Control Engineering Principles and Applications", Leo L. Beranek and Istvan L. Ver, A. Wiley Interscience Publication, pp. 537-541, Aug. 1992.

(Continued)

*Primary Examiner*—Eliseo Ramos-Feliciano
*Assistant Examiner*—Mohamed Charioui

(57) ABSTRACT

An apparatus 10,70 and method is provided that includes a spatial array of unsteady pressure sensors 15-18 placed at predetermined axial locations $X_1$-$X_N$ disposed axially along a pipe 14 for measuring at least one parameter of a solid particle/fluid mixture 12 flowing in the pipe 14. The pressure sensors 15-18 provide acoustic pressure signals $P_1(t)$-$P_N(t)$ to a signal processing unit 30 which determines the speed of sound $a_{mix}$ of the particle/fluid mixture 12 in the pipe 14 using acoustic spatial array signal processing techniques. The primary parameters to be measured include fluid/particle concentration, fluid/particle mixture volumetric flow, and particle size. Frequency based sound speed is determined utilizing a dispersion model to determine the parameters of interest.

46 Claims, 12 Drawing Sheets

U.S. PATENT DOCUMENTS

| | | | |
|---|---|---|---|
| 3,952,578 A | 4/1976 | Jacobs | 73/64.42 |
| 4,080,837 A | 3/1978 | Alexander et al. | 73/61.45 |
| 4,320,659 A | 3/1982 | Lynnworth et al. | 73/589 |
| 4,445,389 A | 5/1984 | Potzick et al. | 73/861.27 |
| 4,520,320 A | 5/1985 | Potzick et al. | 327/7 |
| 4,561,310 A * | 12/1985 | Barnard et al. | 73/861.02 |
| 4,677,305 A | 6/1987 | Ellinger | 250/577 |
| 4,717,159 A | 1/1988 | Alston et al. | 277/314 |
| 4,896,540 A | 1/1990 | Shakkottai et al. | 73/861.02 |
| 4,932,262 A | 6/1990 | Wlodarczyk | 73/705 |
| 5,040,415 A | 8/1991 | Barkhoudarian | 73/198 |
| 5,083,452 A | 1/1992 | Hope | 73/61.49 |
| 5,218,197 A | 6/1993 | Carroll | 250/227.19 |
| 5,289,726 A * | 3/1994 | Miau et al. | 73/861.22 |
| 5,359,897 A | 11/1994 | Hamstead et al. | 73/597 |
| 5,363,342 A | 11/1994 | Layton et al. | 367/149 |
| 5,367,911 A | 11/1994 | Jewell et al. | 73/861.08 |
| 5,398,542 A * | 3/1995 | Vasbinder | 73/40.5 A |
| 5,524,475 A * | 6/1996 | Kolpak et al. | 73/19.03 |
| 5,591,922 A | 1/1997 | Segeral et al. | 73/861.04 |
| 5,708,211 A | 1/1998 | Jepson et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 702/45 |
| 5,845,033 A | 12/1998 | Berthold et al. | 385/12 |
| 5,948,959 A | 9/1999 | Peloquin | 73/1.83 |
| 6,016,702 A | 1/2000 | Maron | 73/705 |
| 6,109,097 A * | 8/2000 | Conrads et al. | 73/61.41 |
| 6,138,512 A | 10/2000 | Roberts et al. | 73/570 |
| 6,202,494 B1 * | 3/2001 | Riebel et al. | 73/861.29 |
| 6,233,374 B1 | 5/2001 | Ogle et al. | 385/13 |
| 6,349,599 B1 | 2/2002 | Lynnworth et al. | 73/644 |
| 6,354,147 B1 * | 3/2002 | Gysling et al. | 73/61.79 |
| 6,378,357 B1 | 4/2002 | Han et al. | 73/54.41 |
| 6,412,353 B1 * | 7/2002 | Kleven et al. | 73/861.22 |
| 6,435,030 B1 | 8/2002 | Gysling et al. | 73/587 |
| 6,442,996 B1 | 9/2002 | Thurston et al. | 73/24.01 |
| 6,443,226 B1 | 9/2002 | Diener et al. | 166/241.6 |
| 6,449,563 B1 * | 9/2002 | Dukhin et al. | 702/22 |
| 6,450,037 B1 | 9/2002 | McGuinn et al. | 73/705 |
| 6,463,813 B1 | 10/2002 | Gysling | 73/862.59 |
| 6,536,291 B1 | 3/2003 | Gysling et al. | 73/861.42 |
| 6,550,342 B2 | 4/2003 | Croteau et al. | 73/800 |
| 6,558,036 B2 | 5/2003 | Gysling et al. | 374/147 |
| 6,587,798 B2 * | 7/2003 | Kersey et al. | 702/50 |
| 6,601,005 B1 * | 7/2003 | Eryurek et al. | 702/104 |
| 6,601,458 B1 | 8/2003 | Gysling et al. | 73/861.04 |
| 6,609,069 B2 | 8/2003 | Gysling | 702/48 |
| 6,658,945 B1 * | 12/2003 | Kleven | 73/861.22 |
| 6,691,584 B2 | 2/2004 | Gysling et al. | 73/861.42 |
| 6,698,297 B2 | 3/2004 | Gysling | 73/861.63 |
| 6,732,575 B2 | 5/2004 | Gysling et al. | 73/61.79 |
| 6,782,150 B2 | 8/2004 | Davis et al. | 385/12 |
| 6,813,962 B2 | 11/2004 | Gysling et al. | 73/861.26 |
| 6,837,332 B1 * | 1/2005 | Rodney | 181/105 |
| 6,862,920 B2 | 3/2005 | Gysling et al. | 73/61.79 |
| 6,889,562 B2 | 5/2005 | Gysling et al. | 73/861.42 |
| 6,898,541 B2 | 5/2005 | Gysling et al. | 702/100 |
| 6,959,604 B2 | 11/2005 | Bryant | 73/705 |
| 2001/0020603 A1 * | 9/2001 | Moorehead et al. | 210/741 |
| 2002/0129662 A1 | 9/2002 | Gysling et al. | 73/861.42 |
| 2003/0038231 A1 | 2/2003 | Bryant et al. | 250/227.14 |
| 2003/0089161 A1 | 5/2003 | Gysling | 73/32 A |
| 2003/0136186 A1 | 7/2003 | Gysling | 73/64.53 |
| 2003/0154036 A1 | 8/2003 | Gysling et al. | 702/25 |
| 2004/0006409 A1 | 1/2004 | Liljenberg et al. | 700/266 |
| 2004/0016284 A1 | 1/2004 | Gysling | 73/1.16 |
| 2004/0074312 A1 | 4/2004 | Gysling | 73/861.04 |

FOREIGN PATENT DOCUMENTS

| | | |
|---|---|---|
| EP | 0290336 | 11/1988 |
| GB | 2210169 | 6/1989 |
| WO | WO 93 14382 | 7/1993 |
| WO | WO 9314382 | 7/1993 |
| WO | WO 00 00793 | 1/2000 |
| WO | WO 0000793 | 1/2000 |
| WO | WO 01 02810 | 1/2001 |
| WO | WO 0102810 | 1/2001 |

OTHER PUBLICATIONS

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

U.S. Appl. No. 60/402,491, filed Aug. 2002, Gysling et al.

"Sonar-Based Volumetric Flow Meter for Pulp and Paper Applications" by: Daniel L. Gysling and Douglas H. Loose—Dec. 3, 2002.

"New Flowmeter Principle", by: Walt Boyes—Published in Flow Controls Magazine—Oct. 2003 Issue.

"Piezoelccric Polymers" by: J.S. Harrison—ICASE Report.

Sonar-Based Volumetric Flow Meter for Chemical and Petrochemical Applications by: Daniel L. Gysling and Douglas H. Loose—Feb. 14, 2003.

"Sound and Sources of Sound" by: A.P. Dowling and J.E. Williams—pp. 224-229.

* cited by examiner

APPARATUS AND METHOD FOR MEASURING PARAMETERS OF A MIXTURE HAVING SOLID PARTICLES SUSPENDED IN A FLUID FLOWING IN A PIPE

CROSS-REFERENCE TO RELATED PATENT APPLICATIONS

This application claims the benefit of U.S. Provisional Application No. 60/351,232, filed Jan. 23, 2002; U.S. Provisional Application No. 60/359,785, filed Feb. 26, 2002; U.S. Provisional Application No. 60/375,847, filed Apr. 24, 2002; U.S. Provisional Application No. 60/425,436, filed Nov. 12, 2002; and U.S. Provisional Application No. 60/426,724, filed Nov. 15, 2002, all of which are incorporated herein by reference in their entirety.

TECHNICAL FIELD

This invention relates to an apparatus for measuring the flow passing within a pipe, and more particularly to an apparatus and method for measuring the speed of sound and/or vortical disturbances propagating in the flow, having particles suspended within a continuous fluid, to determine parameters, such as particle/fluid ratio, particle size and volumetric flow rate of the flow in pipes using acoustic and/or dynamic pressures.

BACKGROUND ART

This invention provides a method to measure parameters of a fluid/particle mixture in a pipe that can be used in many applications, such as in chemical, pharmaceutical, petroleum and power generation industries. In particular, the invention provides a method to measure pulverized coal and air mixtures used in pulverized fuel delivery systems in place in a large percentage of coal fired boilers used in the power generation industry.

Currently, well over 50% of the electricity in the US is generated with coal. While coal is considered a cost effective, abundant resource in the US, the use of coal has been restricted due in large part to environmental concerns. To mitigate this impact, the US Department of Energy and the Power Generation industry have large programs designed to develop technology to reduce the environment effects of burning coal. These Clean Coal Initiatives include technology designed to develop improvements in the combustion process to improve efficiency while reducing pollutants such as unburned carbon, ash, and nitrous oxide (NOx).

The ability to measure the flow rate and composition of the air/coal mixture within the coal pipes is an important aspect of any system or strategy designed to optimize the performance of the PF delivery system. The industry recognizes this and therefore has been developing a wide variety of technologies to perform this measurement. These include probe based and sampling devices, as well as real time meters based on a wide variety of technologies including electrostatic charges, microwaves, and ultrasonic.

SUMMARY OF THE INVENTION

Objects of the present invention include providing a system for measuring the speed of sound propagating through a particle/fluid mixture in pipes in coal fired boiler systems and related processes, for example, to determine particular parameters of the mixture.

According to the present invention, an apparatus for measuring at least one parameter of a particle/fluid mixture in a pipe includes a spatial array of at least two pressure sensors, disposed at different axial locations along the pipe. Each of the pressure sensors measures an unsteady pressure within the pipe at a corresponding axial location. Each of said sensors provides a pressure signal indicative of the unsteady pressure within the pipe at said axial location of a corresponding one of said sensors. A signal processor, responsive to said pressure signals, provides a signal indicative of the at least one parameter of the mixture in the pipe.

According to the present invention, a method for measuring at least one parameter of a particle/fluid mixture in a pipe includes measuring unsteady pressures within the pipe at at least two predetermined axial measurement locations along the pipe to provide a pressure signal indicative of the unsteady pressure within the pipe at each of the at least two predetermined axial measurement locations. Further the method includes calculating the at least one parameter of the particle/fluid mixture in the pipe using the unsteady pressure measured at the axial measurement locations.

The foregoing and other objects, features and advantages of the present invention will become more apparent in light of the following detailed description of exemplary embodiments thereof.

BEST MODE FOR CARRYING OUT THE INVENTION

Figure 1:
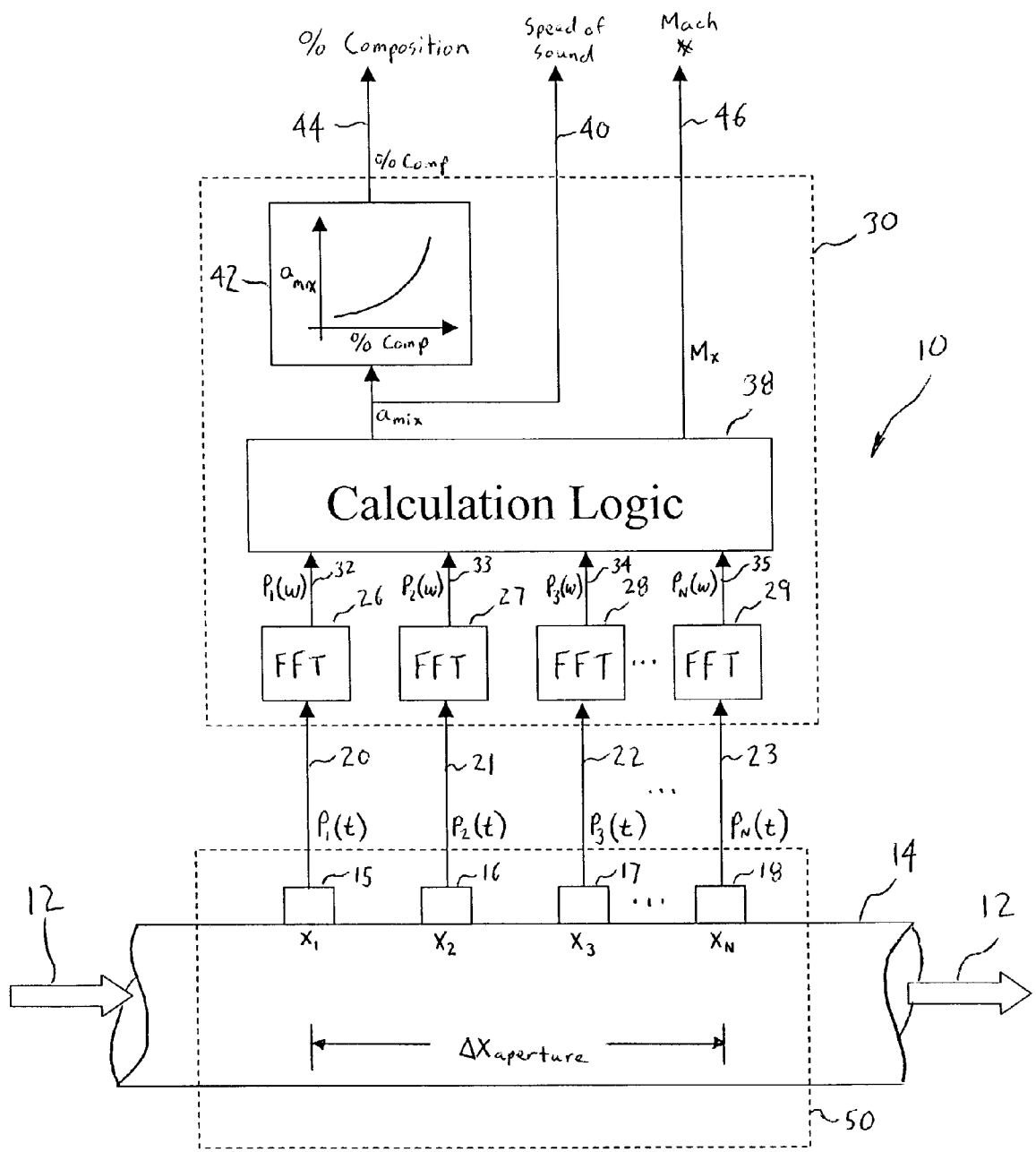
FIG. 1 is a block diagram of a flow meter for measuring the speed of sound of the fluid/particle mixture flowing with a pipe, in accordance with the present invention.
Figure 14:
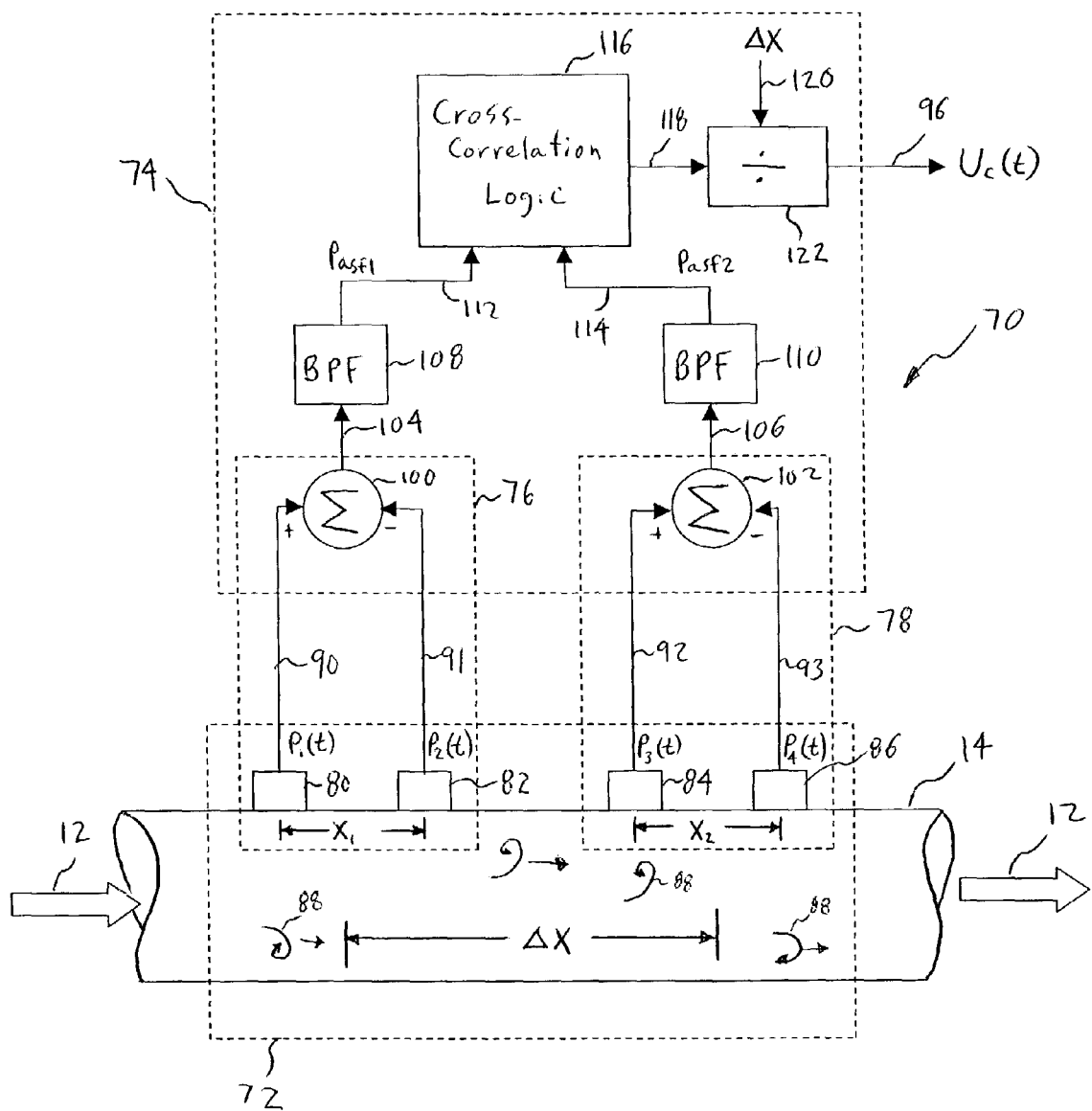
FIG. 14 is a block diagram of a flow meter for measuring the vortical field of the fluid/particle mixture flowing with a pipe, in accordance with the present invention.

Referring to FIGS. 1 and 14, a flow meter 10,70 embodying the present invention is provided that measures a number of parameters/characteristics of a mixture 12 of solid particles suspended within a continuous fluid flowing within a pipe or conduit 14, wherein a fluid is defined as a liquid and/or a gas. The flow meter may be configured and programmed to measure the speed of sound propagating through the mixture or measure the vortical disturbances propagating through the mixture. In some instances, the flow meter 10 may be configured to measure both the speed of sound and the vortical disturbances. Depending on the configuration or embodiment, the flow meter can measure at least one of the following parameters of the mixture flow 12: the fluid/particle concentration (volumetric phase fraction), the volumetric flow rate, the size of the solid particles, the mass flow of the mixture and the velocity of the mixture. To determine any one of these parameters, the flow meter 10,70 measures the unsteady pressures created by the speed of sound (SOS) and/or the vortical disturbances propagating through the mixture flowing in the pipe 14, which will be described in greater detail hereinafter.

The solid particles of the mixture 12 may be of any size, shape and material. For example, the particles may be small in size as in the form of a powder, in a granular form, or greater in size. The flow meter 10,70 can be used in any application that carries solid particles suspended in a fluid through a pipe, such as in chemical, pharmaceutical, petroleum and power generation applications. For example, the present invention is well suited to measure the parameters (e.g. air/coal ratio, particle size) for power generation systems that use pulverized coal to fire the furnace a steam boiler system.

Figure 2:
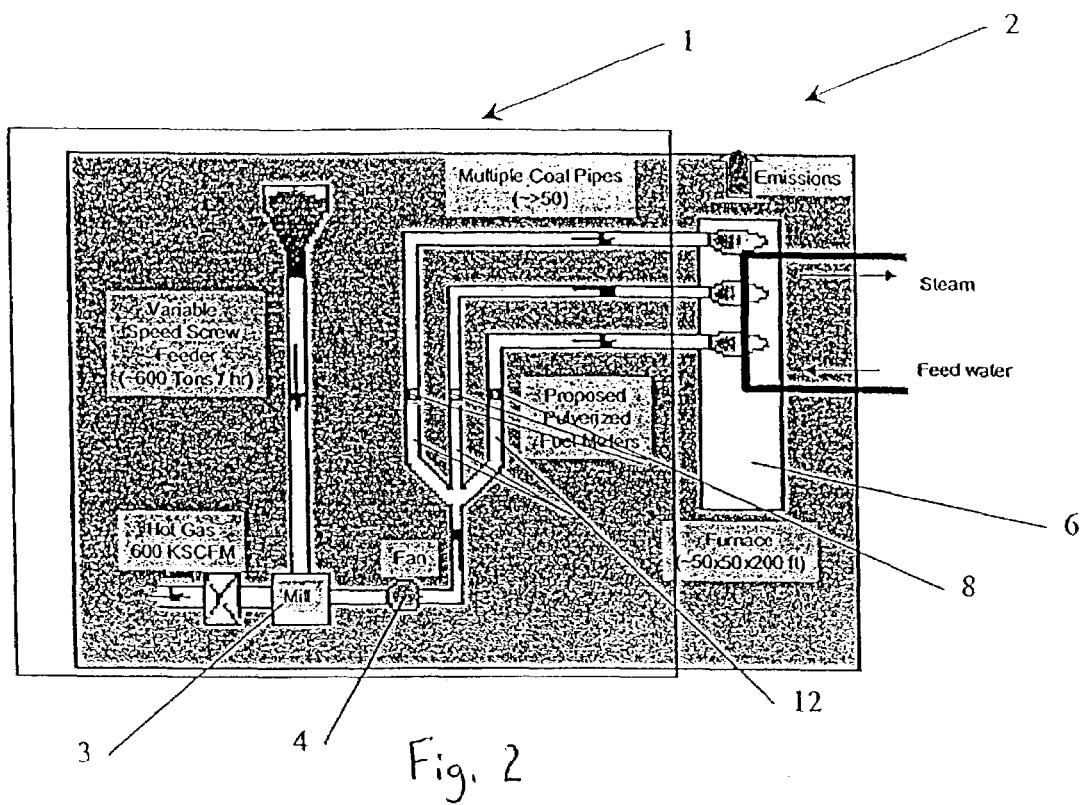
FIG. 2 is a schematic diagram of a pulverized fuel (PF)/air mixture parameter measurement system within a coal fired boiler system, in accordance with the present invention.

As one example, the present invention will be discussed in the context of a Pulverized Fuel (PF) delivery system for power generation, but one will appreciate that the flow meter can be applied to any number of other applications, as discussed hereinbefore. A representative PF delivery system 1 is shown in a coal fired boiler system 2 in FIG. 2. The coal is pulverized in a mill 3 and entrained in air produced by many means, such as a fan 4 to transport the PF/air mixture via pipes 12 for delivery to the furnace 6. Typical furnaces can have >50 coal pipes, each 12-20 inch in diameter. Typically, a large utility boiler >300 Mw, can have 4-11 pulverizing mills feeding the furnace. The ability of the PF delivery system to deliver the proper amount of fuel and air to the furnace through these multiple coal pipes, both collectively and individually, has a strong influence on the performance and emissions from the coal fired boiler.

As is known, non-uniformities in the PF delivery system 1 can result in variation of the fuel to air ratios, causing hot spots, regions of high NOx generation, and unburned fuel. The connection between performance of a PF fuel delivery system 1 and a boiler system 2 is well recognized. The flow meter 10 embodying the present invention is capable of measuring the fuel to air ratio and particle size of the pulverized coal provided to the furnace to thereby provide feedback to the operator to provide more efficient combustion of the coal.

As described hereinbefore, the flow meter 10,70 of the present invention may be configured and programmed to measure and process the detected unsteady pressures $P_1(t)$-$P_N(t)$ created by acoustic waves and/or vortical disturbances propagating through the mixture to determine parameters of the mixture flow 12. One such flow meter 10 is shown in FIG. 1 that measures the speed of sound (SOS) of one-dimensional sound waves propagating through the fluid/particle mixture to determine the composition the mixture, namely the liquid/particle ratio of the mixture. The flow meter is also capable of determining the average size of the particles, velocity of the mixture, and the volumetric flow rate of the mixture. It is known that sound propagates through various mediums at various speeds in such fields as SONAR and RADAR fields. The speed of sound of a mixture within a pipe 14 may be determined using a number of known techniques, such as those set forth in U.S. patent application Ser. No. 09/344,094, entitled "Fluid Parameter Measurement in Pipes Using Acoustic Pressures", filed Jun. 25, 1999, and U.S. patent application Ser. No. 10/007,749, entitled "Fluid Parameter Measurement in Pipes Using Acoustic Pressures", filed Nov. 7, 2001, each of which are incorporated herein by reference. The present invention utilizes at least one flow meter 10 to determine various parameters of the liquid/particle mixture, wherein one of the parameters is the speed at which sound travels within the mixture pipe system as will be more fully described herein below.

In accordance with the present invention, the speed of sound propagating through the mixture 12 is measured by passively listening to the flow with an array of unsteady pressure sensors to determine the speed at which one-dimensional compression waves propagate through a liquid/particle mixture contained within the pipe 14.

As shown in FIG. 1, the flow meter 10 has an array of at least three acoustic pressure sensors 15,16,17, located at three locations $x_1, x_2, x_3$ axially along the pipe 14. One will appreciate that the sensor array may include more than three pressure sensors as depicted by pressure sensor 18 at location $X_N$. The pressure generated by the acoustic waves may be measured through holes in the pipe 14 ported to external pressure sensors 15-18 or by other techniques discussed hereinafter. The pressure sensors 15-18 provide pressure time-varying signals $P_1(t), P_2(t), P_3(t), P_N(t)$ on lines 20,21, 22,23 to a signal processing unit 30 to known Fast Fourier Transform (FFT) logics 26,27,28,29, respectively. The FFT logics 26-29 calculate the Fourier transform of the time-based input signals $P_1(t)-P_N(t)$ and provide complex frequency domain (or frequency based) signals $P_1(\omega), P_2(\omega), P_3(\omega), P_N(\omega)$ on lines 32,33,34,35 indicative of the frequency content of the input signals. Instead of FFT's, any other technique for obtaining the frequency domain characteristics of the signals $P_1(t)-P_N(t)$, may be used. For example, the cross-spectral density and the power spectral density may be used to form a frequency domain transfer functions (or frequency response or ratios) discussed hereinafter.

The frequency signals $P_1(\omega)-P_N(\omega)$ are fed to $a_{mix}$-Mx Calculation Logic 38 which provides a signal to line 40 indicative of the speed of sound of the mixture $a_{mix}$ (discussed more hereinafter). The $a_{mix}$ signal is provided to map (or equation) logic 42, which converts $a_{mix}$ to a percent composition of the PF/air mixture and provides a % Comp signal to line 44 indicative thereof (as discussed hereinafter). Also, if the Mach number Mx is not neglible and is desired, the calculation logic 40 may also provide a signal Mx to line 46 indicative of the Mach number Mx.

More specifically, for planar one-dimensional acoustic waves in a homogenous mixture, it is known that the acoustic pressure field P(x,t) at a location x along a pipe, where the wavelength $\lambda$ of the acoustic waves to be measured is long compared to the diameter d of the pipe 12 (i.e., $\lambda/d>>1$), may be expressed as a superposition of a right traveling wave and a left traveling wave, as follows:

$$P(x,t) = (Ae^{-ik_r x} + Be^{+ik_l x})e^{i\omega t} \qquad \text{Eq. 1}$$

where A,B are the frequency-based complex amplitudes of the right and left traveling waves, respectively, x is the pressure measurement location along a pipe, $\omega$ is frequency (in rad/sec, where $\omega = 2\pi f$), and $k_r, k_l$ are wave numbers for the right and left travelling waves, respectively, which are defined as:

$$k_r \equiv \left(\frac{\omega}{a_{mix}}\right)\frac{1}{1+M_x} \text{ and } k_l \equiv \left(\frac{\omega}{a_{mix}}\right)\frac{1}{1-M_x} \qquad \text{Eq. 2}$$

where $a_{mix}$ is the speed of sound of the mixture in the pipe, $\omega$ is frequency (in rad/sec), and $M_x$ is the axial Mach number of the flow of the mixture within the pipe, where:

$$M_x \equiv \frac{V_{mix}}{a_{mix}} \qquad \text{Eq. 3}$$

where V mix is the axial velocity of the mixture. For non-homogenous mixtures, the axial Mach number represents the average velocity of the mixture and the low frequency acoustic field description remains substantially unaltered.

The data from the array of sensors may be processed in any domain, including the frequency/spatial domain, the temporal/spatial domain, the temporal/wave-number domain or the wave-number/frequency (k-$\omega$) domain. As such, any known array processing technique in any of these or other related domains may be used if desired.

Also, some or all of the functions within the signal processing unit 30 may be implemented in software (using a microprocessor or computer) and/or firmware, or may be implemented using analog and/or digital hardware, having sufficient memory, interfaces, and capacity to perform the functions described herein.

Acoustic pressure sensors 15-18 sense acoustic pressure signals that, as measured, are lower frequency (and longer wavelength) signals than those used for ultrasonic flow meters of the prior art, and thus the current invention is more tolerant to inhomogeneities in the flow, such as roping and other time and space domain inhomogeneities within the flow, even where entrenchment or coal "roping" is unlikely such as following a bend. The term "roping" is a term known to those skilled in this art which represents a form of severe spatial and temporal mal-distribution induced in mixture flows of widely different component densities. It is a condition where a large portion of the coal flow is in a band running along one side of pipe 14.

In addition, the present invention incorporates the compliance of the pipe 14 to determine the effective speed of sound of the pipe/PF/air mixture system. The acoustic pressure signals $P_1(t)-P_N(t)$ are generated within the PF/air mixture of the pipe 14 by a variety of non-discrete sources such as remote machinery, mills, fans 4 (FIG. 2), valves, elbows, as well as the PF/air mixture flow itself. It is this last source, the PF/air mixture 12 flowing within the pipe 14, which is a generic source of acoustic noise that assures a minimum level of acoustics for any PF/air mixture piping systems for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the flow meter 10 passively listens to the mixture flow 12, the present invention contemplates adding an acoustic source to inject a desire acoustic wave into the flow to be measured, such as by compressing, vibrating and/or tapping the pipe, to name a few examples.

For certain types of pressure sensors, e.g., pipe strain sensors, accelerometers, velocity sensors or displacement sensors, discussed hereinafter, it may be desirable for the pipe 14 to exhibit a certain amount of pipe compliance.

Alternatively, to minimize any error effects (and the need for the corresponding calibration) caused by pipe compliance, the axial test section 50 of the pipe 14 along where the sensors 15-18 are located may be made as rigid as possible. To achieve the desired rigidity, the thickness of the wall of the test section 50 may be made to have a predetermined thickness, or the test section 50 may be made of a very rigid material, e.g., steel, titanium, Kevlar®, ceramic, or other material with a high modulus.

It is within the scope of the present that the pressure sensor spacing may be known or arbitrary and that as few as two sensors are required if certain information is known about the acoustic properties of the PF/air mixture piping system. The pressure sensors are spaced sufficiently such that the entire length of the array (aperature) is at least a significant fraction of the measured wavelength of the acoustic waves being measured. As will be described in greater detail, the acoustic wavelength to be measured is a function of at least the size and mass of the particles, and the viscosity of the fluid. The greater the size and mass of the particles and/or the less viscous the fluid, the greater the spacing of the sensors is needed. Conversely, the smaller the size and mass of the particles and/or the more viscous the fluid, the shorter the spacing of the sensors is needed.

As discussed, the flow meter 10 measures the speed of sound of one-dimensional sound waves propagating through the fluid/particle mixture to determine the composition of the mixture. Specifically, the speed of sound propagating through dilute solid/air mixtures can be directly related to the mass fraction particles of the flow. A typical PF fuel delivery system 1 may operate with an air to coal mass ratio of 1.5 to 2.5. Typically, PF delivery systems operate with an air-to-coal mass ratio of 1.5 to 2.5 with coal density of 1200 to 1400 kg/m³ compared to 1.2 kg/m³ for air at standard atmospheric conditions. Thus, meeting the desired mass ratio results in a very dilute mixture of coal on a volumetric basis, on the order of one part in 1000 by volume.

Assuming that the particles of coal are small enough and the acoustic frequencies and the frequencies of perturbations associated with the acoustics are low enough for the solid particles to exhibit negligible slip (both steady and unsteady), the sound speed can be assumed to be non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

Including the effect of the compliance introduced by the conduit 12 (in this case a circular pipe of modulus E, radius R and wall thickness t)

$$\frac{1}{\rho_{mix} a_{measured}^2} = \frac{1}{\rho_{mix} a_{mix}^2} + \sigma \text{ where } \sigma \equiv \frac{2R}{Et}$$

Figure 4:
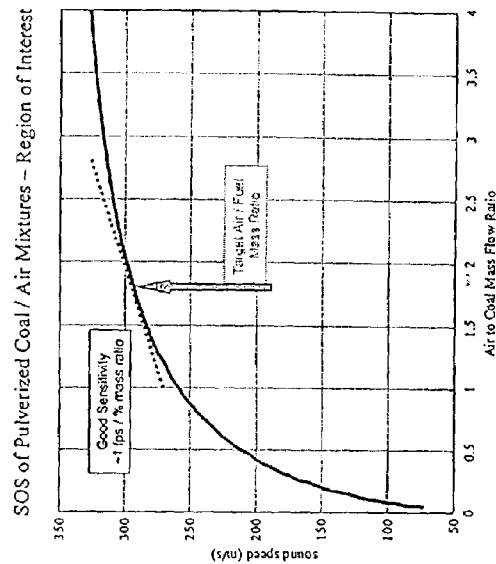
FIG. 4 is a plot of the speed of sound of a mixture versus the frequency in air/coal mass flow ratio, in accordance with the present invention.

Utilizing the relations above, the speed at which sound travels within the piping system of a representative coal/air mixtures is shown in FIG. 4 as a function of air/coal mass ratio. For this example, the pure air was assumed to have a density of 1.2 kg/m^3 and a sound speed of 365.9 m/s and the coal was assumed to have a density of 1400 kg/m^3 and a sound speed of 2439 m/s. As shown, the effect of increasing coal fraction, i.e. decreasing air/coal ratio is to decrease the sound speed. Physically, adding coal particles effectively mass loads the mixture, while not appreciably changing the compressibility of the air. Over the parameter range of interest, the relation between mixture sound speed and air/coal ratio is well behaved and monatomic.

While the calibration curves based on predictions from first principles are encouraging, using empirical data mapping from sound speed to air/coal ratio may result in improved accuracy of the present invention to measure the air/coal fractions of the mixture.

However, it has been discovered that the physical properties of pulverized coal/air mixtures are generally such that there will be velocity slip at all but very low frequencies (on the order of <1-2 Hz for nominally 50 µm coal particles in air).

Figure 3:
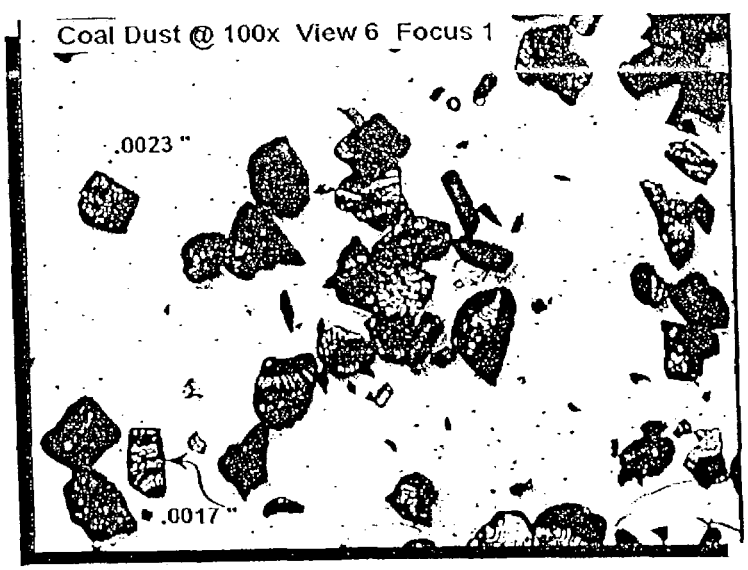
FIG. 3 is a magnified photograph showing particle size of coal typical of the system shown in FIG. 2.
Figure 5:
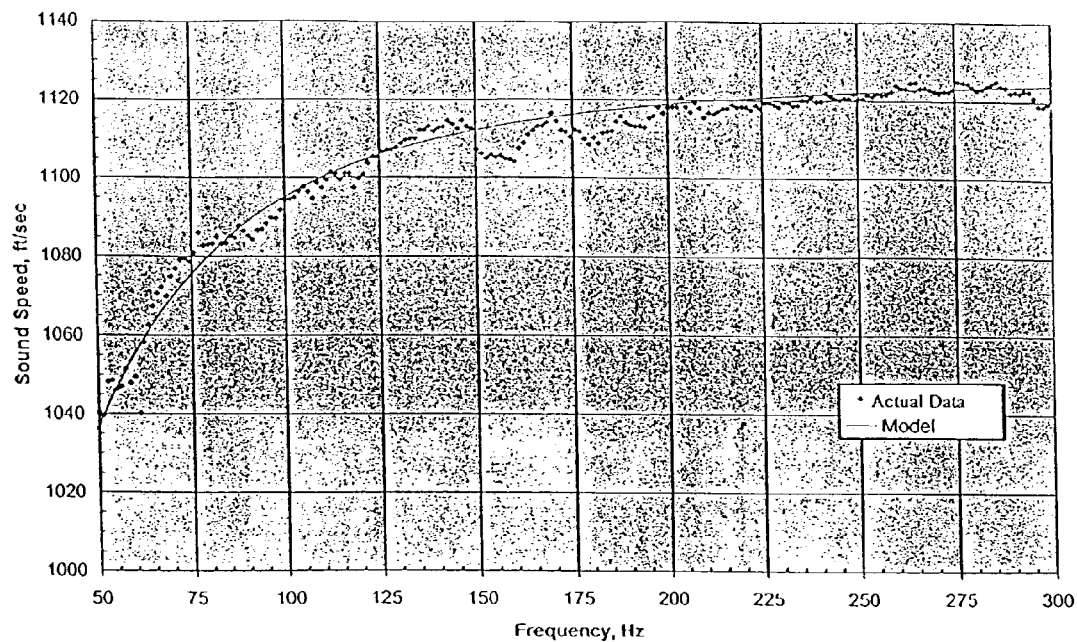
FIG. 5 is a plot of actual data and a model of the speed of sound as a function of frequency for air/coal mixtures, in accordance with the present invention.

FIG. 5 shows the measured speed of sound as a function of frequency for an actual coal/air mixture 12. The sound speed was measured utilizing passive listening techniques of the present invention as described herein. The frequency dependence of the sound speed was determined by applying a Capon array-processing algorithm at multiple narrow frequency ranges between 50-300 Hz thereby determining a frequency specific acoustic propagation velocity. In this particular example, the data was obtained wherein the coal/air mixture was flowing at nominally 100 ft/sec with an air-to-coal mass ratio equal to 1.8. The coal particles were nominally 50 µm in size, representative of pulverized coal typically used in power generation and other industrial applications. A magnified view of the coal particles that were used for this test is shown in FIG. 3.

Further shown in FIG. 5, the sound speed increases with increasing frequency and asymptotes toward a constant value. The sound speed asymptote at higher frequency is essentially the sound speed of air only with no influence of the suspended particles. Also, it is apparent that the sound speed of the coal/air mixture has not reached the quasi-steady limit at the lowest frequency for which sound speed was measured. The sound speed is continuing to decrease at the lower frequency limit. An important discovery of the present invention is that the speed at which sound propagates through dilute particles suspended in a continuous fluid is said to be dispersive. As defined herein, the speed at which acoustic waves propagate through dispersive mixtures varies with frequency.

Figure 6:
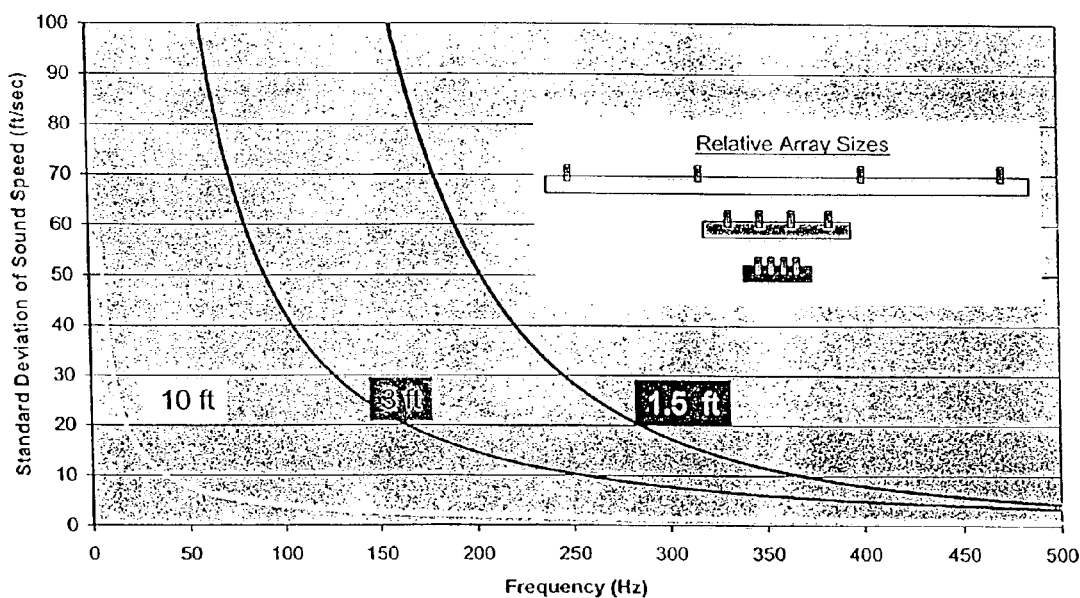
FIG. 6 is a plot showing the standard deviation of sound speed versus frequency for various arrays of a PF/air mixture parameter measurement system, in accordance with the present invention.

Measuring the sound speed of a mixture 12 at progressively lower and lower frequencies becomes inherently less accurate as the total length of the array of pressure sensors 15-18 ($\Delta x_{aperature}$), which define the aperature of the array, becomes small compared to the wavelength of the acoustics. In general, the aperture should be at least a significant fraction of a wavelength of the sound speed of interest. In a particular embodiment sound speed data was recorded with an array of four sensors, spaced at 12 inches, for a total aperture of three feet. At 50 Hz, a 1000 ft/sec sound wave has a wavelength of 20 ft. Thus, the aperture of this particular array (approx. 36 inches) spanned only 3/20ths of a wavelength, and the array's ability to accurately resolve sound speeds below this was clearly impaired. It is an important aspect of the present invention that the ability to resolve sound speed at low frequencies is directly related to aperture of the array. Consequently longer arrays are used to resolve sound speeds at lower frequencies. As shown in FIG. 6, the standard deviation associated with determining the speed of sound in air is shown as a function of frequency for three arrays of varying aperture, namely 1.5 ft, 3 ft and 10 ft.

Given the practical constraints in accurately measuring sound speeds at ultra-low frequencies, the data suggests that utilizing a quasi-steady model to interpret the relationship between sound speed, measured at frequencies above those at which the quasi-steady model is applicable, and the air-to-fuel ratio would be problematic, and may, in fact, be impractical. Thus, the key to understanding and interpreting the composition of coal/air mixtures through sound speed measurements lies in the dispersive characteristics of the coal/air mixture.

In accordance with the present invention the dispersive nature of the system utilizes a first principles model of the interaction between the air and particles. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous fluid phase and that of the particles. The drag force on the particles by the continuous fluid is modeled by a force proportional to the difference between the local fluid velocity and that of the fluid particles and is balanced by inertial force:

$$F_{drag} = K(U_f - U_p) = \rho_p v_p \frac{\partial U_p}{\partial t}$$

where K=proportionality constant, $U_f$=fluid velocity, $U_p$=particle velocity, $\rho_p$=particle density and $v_p$=particle volume.

The effect of the force on the continuous fluid phase by the fluid particles is modeled as a force term in the axial momentum equation. The axial momentum equation for a control volume of area A and length $\Delta x$ is given by:

$$P_x - P_{x+\Delta x} - K(U_f - U_p)\left\{\frac{\phi_p \Delta x}{v_p}\right\} = \frac{\partial}{\partial t}(\rho_f U_f \Delta x)$$

where P=pressure at locations x and $\Delta x$, $\phi_p$=volume fraction of the particles, $\rho_f$=fluid density.

The particle drag force is given by:

$$F_{drag} = K(U_f - U_p) = C_d A_p \frac{1}{2} \rho_f (U_f - U_p)^2$$

where $C_d$=drag coefficient, $A_p$=frontal area of particle and $\rho_f$=fluid density.

Using Stokes law for drag on a sphere at low Reynold's number gives the drag coefficient as:

$$C_d = \frac{24}{Re} = \frac{24\mu}{\rho_f(U_f - U_p)D_p}$$

where $D_p$=particle diameter and $\mu$=fluid viscosity.

Solving for K in this model yields:

$$K = 3\pi\mu D_p$$

Using the above relations and 1-dimensional acoustic modeling techniques, the following relation can be derived for the dispersive behavior of an idealized fluid particle mixture.

$$a_{mix}(\omega) = a_f \sqrt{\frac{1}{1 + \frac{\varphi_p \rho_p}{\rho_f\left(1 + \omega^2 \frac{\rho_p^2 v_p^2}{K^2}\right)}}}$$

In the above relation, the fluid SOS, density ($\rho$) and viscosity ($\phi$) are those of the pure phase fluid, $v_p$ is the volume of individual particles and $\phi_p$ is the volumetric phase fraction of the particles in the mixture.

Figure 7:
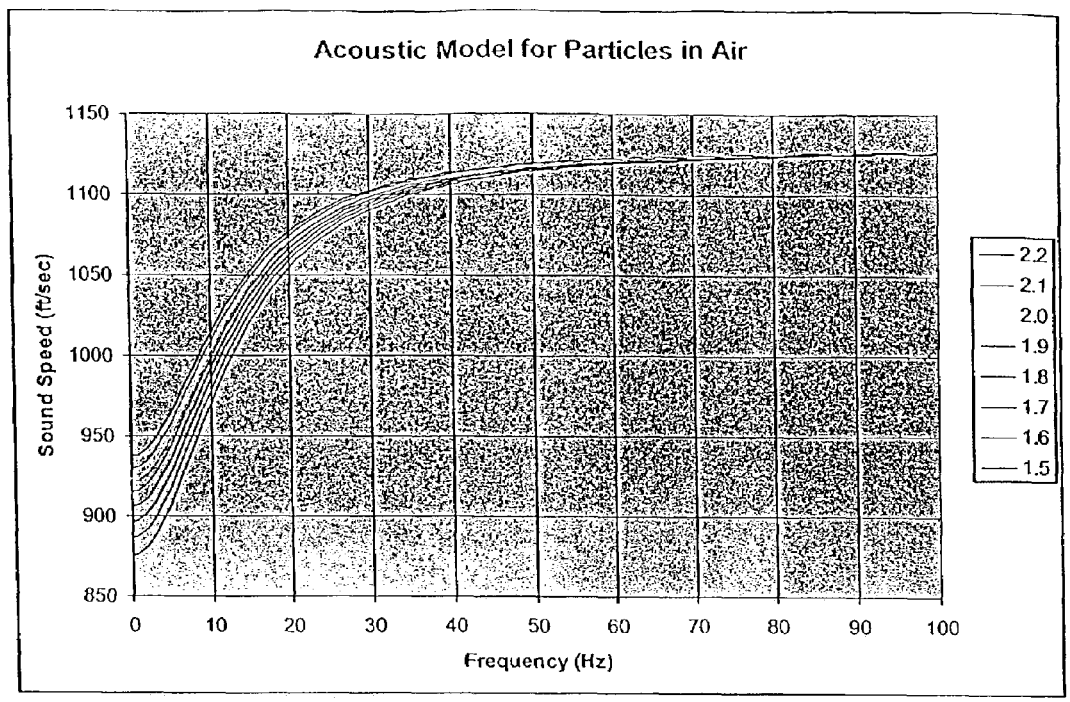
FIG. 7 is a plot of sound speed as a function of frequency for air/coal mixtures with fixed particle size (50 mm) and varying air-to-fuel mass Ratio in accordance with the present invention.
Figure 8:
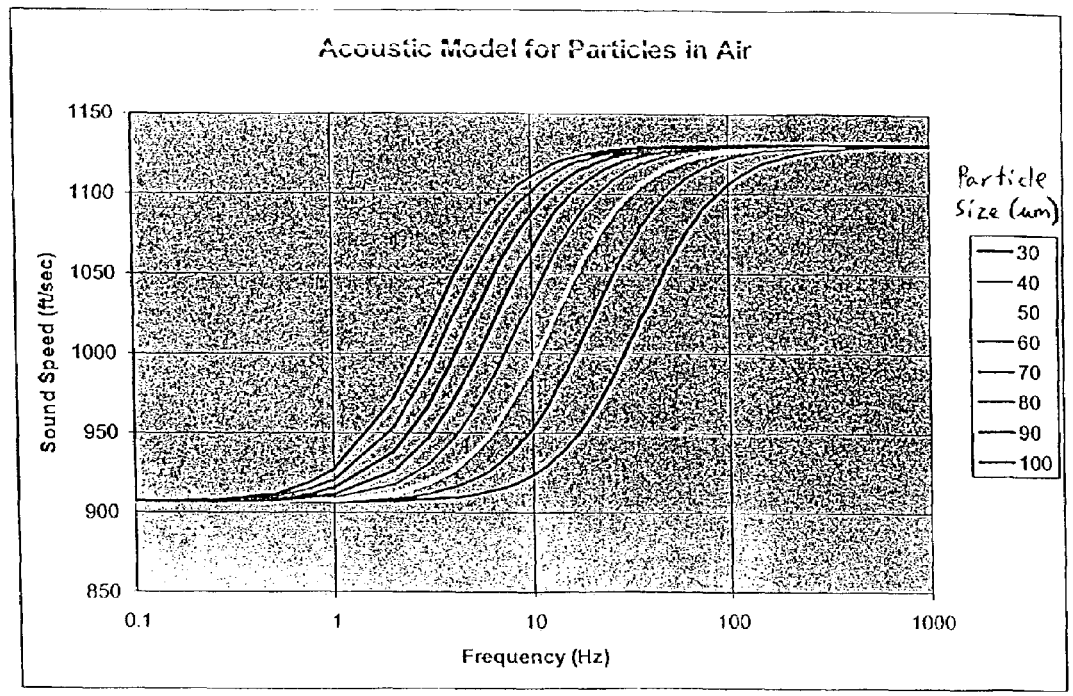
FIG. 8 is a plot of sound speed as a function of frequency for air/coal mixtures with varying particle size where the air-to-fuel mass ratio is equal to 1.8 in accordance with the present invention.

Two parameters of primary interest in pulverized coal measurements are particle size and air-to-fuel mass ratio. To this end, it is of interest to examine the dispersive characteristics of the mixture as a function of these two variables. FIGS. 7 and 8 show the dispersive behavior for coal/air mixtures with parameters typical of those used in pulverized coal deliver systems.

In particular FIG. 7 shows the predicted behavior for nominally 50 µm size coal in air for a range of air-to-fuel ratios. As shown, the effect of air-to-fuel ratio is well defined in the low frequency limit. However, the effect of the air-to-fuel ratio becomes indistinguishable at higher frequencies, approaching the sound speed of the pure air at high frequencies (above ~100 Hz).

Similarly, FIG. 8 shows the predicted behavior for a coal/air mixture with an air-to-fuel ratio of 1.8 with varying particle size. This figure illustrates that particle size has no influence on either the low frequency limit (quasi-steady) sound speed, or on the high frequency limit of the sound speed. However, particle size does have a pronounced effect in the transition region.

FIGS. 7 and 8 illustrate an important aspect of the present invention. Namely, that the dispersive properties of dilute mixtures of particles suspended in a continuous fluid can be broadly classified into three frequency regimes: low frequency range, high frequency range and a transitional frequency range. Although the effect of particle size and air-to-fuel ratio are inter-related, the predominant effect of air-to-fuel ratio is to determine the low frequency limit of the sound speed to be measured and the predominate effect of particle size is to determine the frequency range of the transitional regions. As particle size increases, the frequency at which the dispersive properties appear decreases. For typical pulverized coal applications, this transitional region begins at fairly low frequencies, ~2 Hz for 50 µm size particles.

In the low frequency regime, the particles exhibit negligible slip with the fluid. The frequency range for which the no-slip, quasi-steady approximation is valid is a function of a variety of parameters including particle size, continuous phase viscosity, particle shape and particle density.

The quasi-steady sound speed is given by the low frequency limit of the above relation, where AFR is air/fuel ratio:

$$a_{mix}(\omega \to 0) = a_f * \sqrt{\frac{1}{1 + \frac{\varphi_p \rho_p}{\rho_f}}} \cong a_f * \sqrt{\frac{1}{1 + \frac{1}{AFR}}}$$

Figure 9:
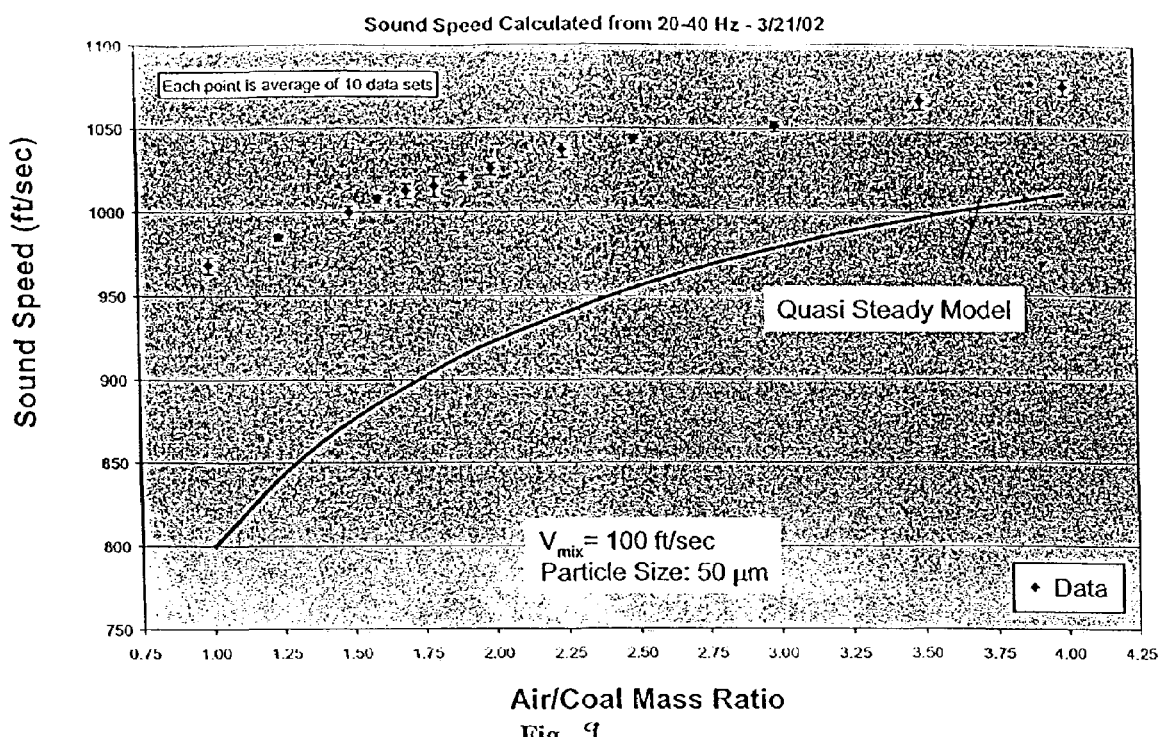
FIG. 9 is a plot of sound speed as function of air/coal ratio in accordance with the present invention.

Note that particle size does not affect the low frequency limit of the sound speed. Referring to FIG. 9, the sound speed was measured using an embodiment of the present invention having eight sensors at 20.5 inch spacing, averaged from 20-40 Hz, for a range of air-to-coal mass ratios. The sound speed predicted for the coal/air mixtures using the quasi-steady model are also presented. As shown, although the general trend is captured, i.e. sound speed decreases with increased coal loading, the error is significant, rendering a first principle interpretation, based on a quasi-steady model inadequate.

In the high frequency limit, the dispersion relation predicts the sound speed with asymptote towards the sound speed of the pure fluid.

$$a_{mix}(\omega ==> \infty) = a_{fluid}$$

Interestingly, the high frequency limit is independent of both particle size and air-to-fuel ratio.

Given the difficulties measuring sufficiently low frequencies to apply the quasi-steady model and recognizing that the high frequency sound speed contains no direct information on either particle size or air-to-fuel ratio, it becomes apparent that the dispersive characteristics of the coal/air mixture should be utilized to determine particle size and air-to-fuel ratio based on speed of sound measurements.

As described hereinbefore, the flow meter 10 of the present invention includes the ability to accurately determine the average particle size of the coal in the PF/air mixture within the pipe 14 and the air to fuel ratio. Provided there is no appreciable slip between the air and the solid coal particle, the propagation of one dimensional sound wave through multiphase mixtures is influenced by the effective mass and the effective compressibility of the mixture. For an air transport system, the degree to which the no-slip assumption applies is a strong function of particle size and frequency. In the limit of small particles and low frequency, the no-slip assumption is valid. As the size of the particles increases and the frequency of the sound waves increase, the non-slip assumption becomes increasing less valid. For a given average coal particle size, the increase in slip with frequency causes dispersion, or, in other words, the sound speed of the mixture to change with frequency. With appropriate calibration the dispersive characteristic of a mixture will provide a measurement of the average particle size, as well as, the air to fuel ratio (particle/fluid ratio) of the mixture.

Using the model described above, which yields the equation shown below, and experimentally determined sound speed as function of frequency, the present invention includes an optimization procedure to simultaneously determine particles size and AFR in coal/air mixtures:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

Figure 10:
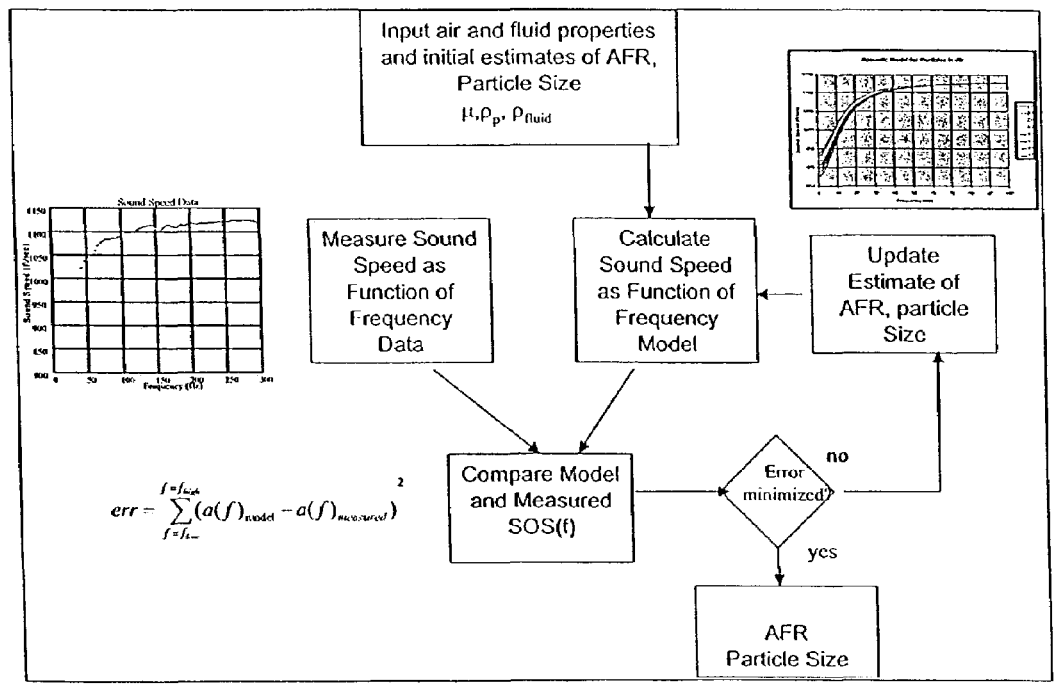
FIG. 10 is a flow diagram of an optimization procedure employed to determine air-to-fuel ratio and particle size from analytical model and experimentally determined dispersive speed of sound data in accordance with the present invention.

Referring to FIG. 10 there is shown an optimization procedure in accordance with the present invention in which the free parameters of an analytical model are optimized to minimize an error function. For illustration purposes, the error function utilized is the sum of the differences of the sound speeds between an analytical model and the experimentally determined sound speed as a function of frequency:

$$err = \sum_{f=f_{low}}^{f=f_{high}} (a(f)_{model} - a(f)_{measured})^2$$

Figure 11:
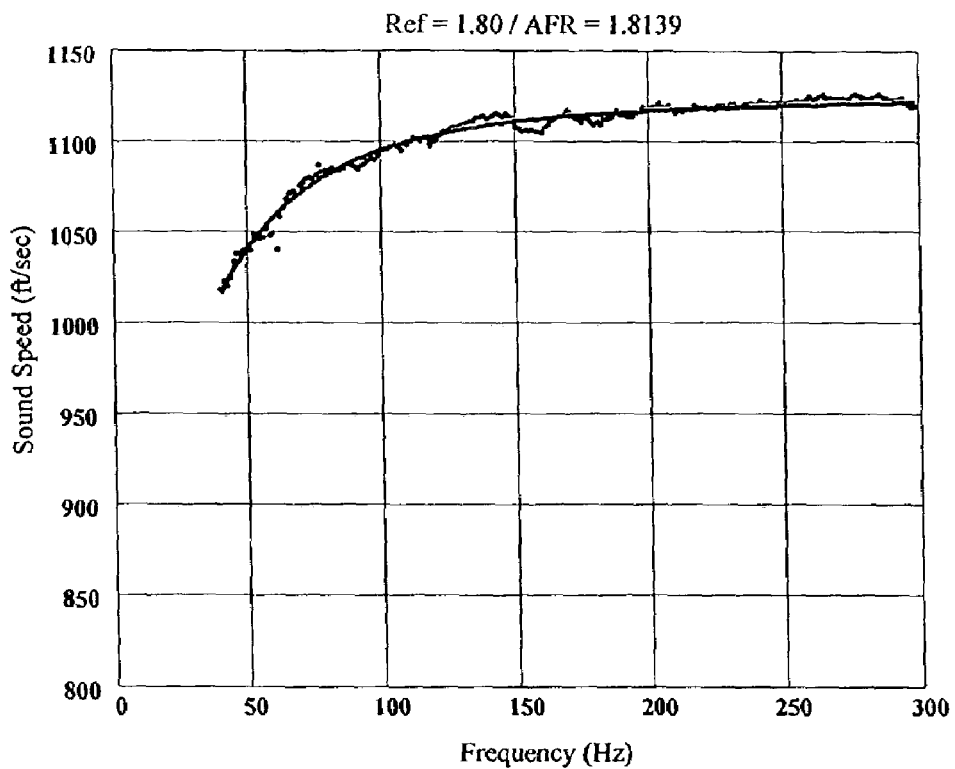
FIG. 11 is a plot of the results of the optimization procedure of FIG. 10 applied to data recorded from an array of sensors listening to flow in a six inch circular duct, 50 μm particle size, 100 ft/sec air flow rate with an air-to-fuel ratio of 1.8.

The results of the optimization procedure applied to data recorded from an array of sensors listening to flow in a six inch circular duct, 50 μm particle size, 100 ft/sec air flow rate with an air-to-fuel ratio of 1.8 is shown in FIG. 11. The measured and optimized-model-predicted sound speed is shown. As shown, the model captures the transitional frequency range well and provides a good estimate of the air-to-fuel ratio.

Figure 12:
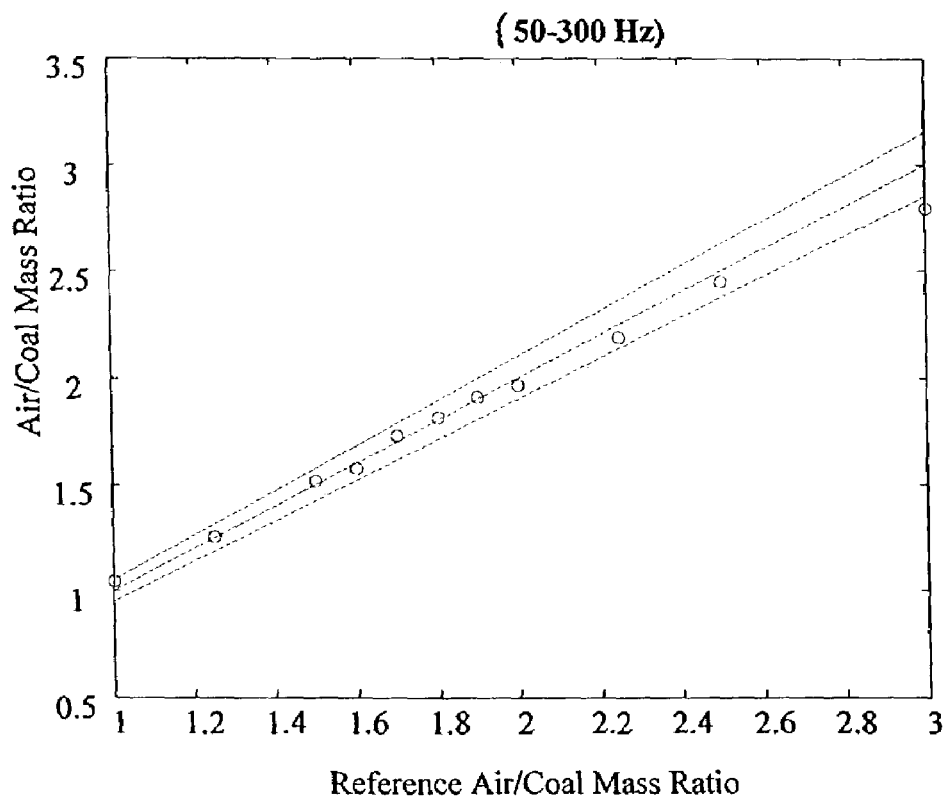
FIG. 12 is a plot of the results of the optimization procedure of FIG. 10 applied to a series of data sets with varying air-to-fuel ratio.

The results of the optimization procedure applied to a series of data sets with varying air-to-fuel ratio is shown in FIG. 12. Note for this optimization the particle size was held constant over the range of data sets.

In addition to measuring the fluid to particle ratio of the mixture 12 and particle size within a pipe 14 using the measured speed of sound, the flow meter 10 further includes the ability to measure of volumetric flow rate of the mixture by comparing the difference of the speed of one dimensional sound waves propagating with and against the mean flow.

This method of determining the volumetric flow rate of the particle/fluid mixture 12 within pipe 14 relies on the interaction of the mean flow with the acoustic pressure field. The interaction results in sound waves propagating with the mean flow traveling at the speed of sound (if the particle/liquid mixture were not flowing) plus the convection velocity and, conversely, sound waves traveling against the mean flow propagating at the speed of sound minus the convection velocity. That is, $$a_R = a_{mix} + \mu$$

$$a_L = a_{mix} - \mu$$

where $a_R$=velocity of a right traveling acoustic wave relative to a stationary observer (i.e. the pipe 14), $a_L$=velocity of a left traveling acoustic wave apparent to a stationary observer, $a_{mix}$=fluid speed of sound (if the fluid were not flowing) and $\mu$=the mean flow velocity (assumed to be flowing from left to right in this instance). Combining these two equations yields an equation for the mean velocity, $$u = \frac{a_R - a_L}{2}$$

Therefore, by measuring the propagation velocity of acoustic waves in both directions relative to the stationary pipe as described hereinbefore, the mean flow velocity can be calculated by multiplying the mean flow velocity by the cross-sectional area of the pipe 14.

The practicality of using this method to determine the mean flow is predicated on the ability to resolve the sound speed in both directions with sufficient accuracy to determine the volumetric flow. For typical liquid measurements, flow velocities are typically at ~10 ft/sec and sound speeds of ~4000 ft/sec. Thus axial mach numbers are on the order of 10/4000 of 0.0025. For a +/−10% accuracy in flow rate (+/−1 ft/sec), the sound speed of the upstream and downstream propagating waves would need to be resolved to +/−0.5/4000 or 1 part in 8,000.

However, for PF/air mixture flows, axial flow velocities are nominally around 70 ft/sec with no flow sound speeds of ~700 ft/sec. This results in mach numbers of ~0.1, approximately 2 orders of magnitude greater than typical liquid flows. For pulverized fuel flows, to resolve the flow rate to 10% accuracy (or +/−7 ft/sec), one would have to resolve the sound speed to +/−3.5 ft/sec, or 3.5/700 or 1 part in 200.

For the sound speed measurement, the flow meter 10 utilizes similar processing algorithms as those employed herein before. The temporal and spatial frequency content of sound propagating within the process piping 14 is related through a dispersion relationship.

$$\omega = \frac{k}{a_{mix}}$$

The wave number is k, which is defined as $k=2\pi/\lambda$, $\omega$ is the temporal frequency in rad/sec, and $a_{mix}$ is the speed at which sound propagates within the process piping. For this cases where sound propagates in both directions, the acoustic power is located along two acoustic ridges, one for the sound traveling with the flow at a speed of $a_{mix}+V_{mix}$ and one for the sound traveling against the flow at a speed of $a_{mix}-V_{mix}$.

Figure 13:
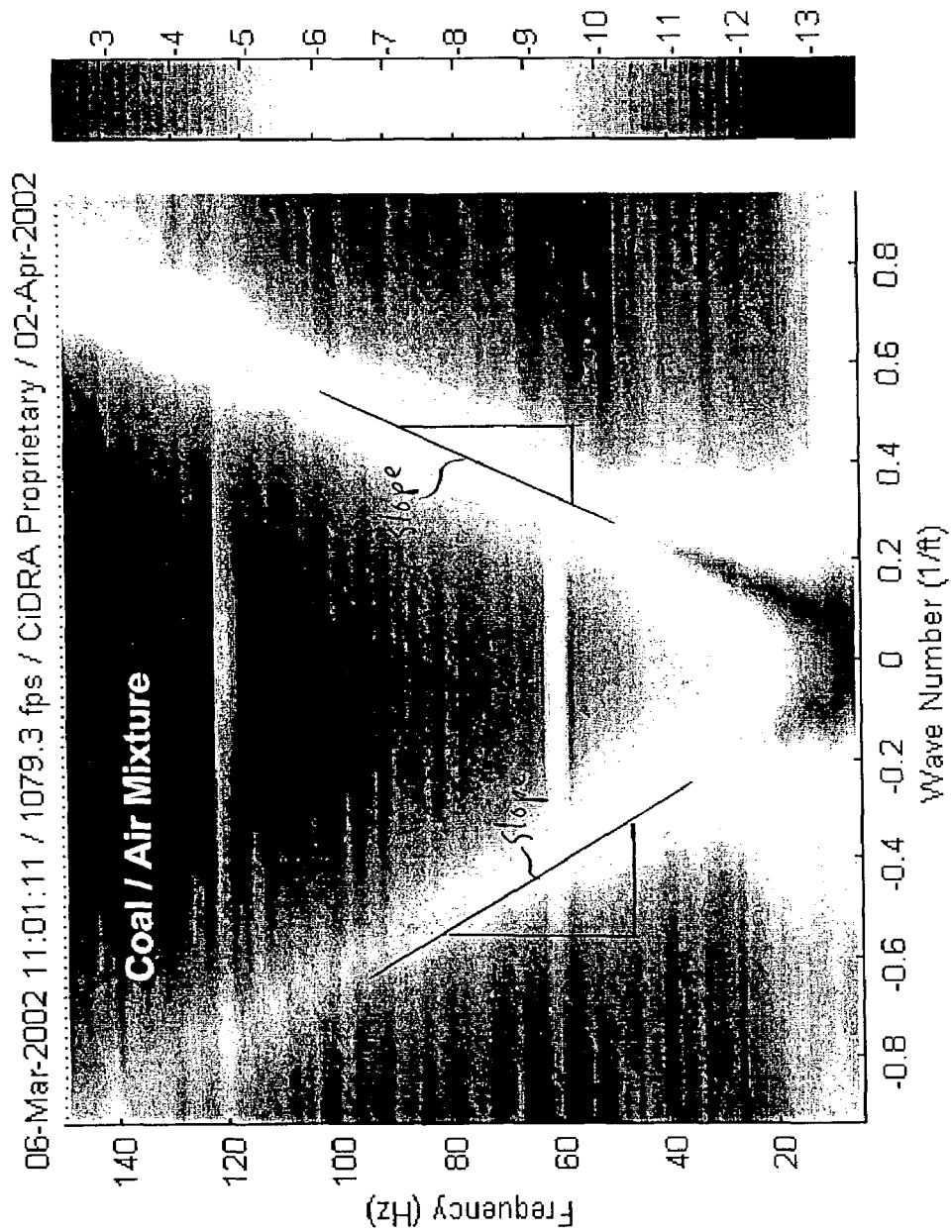
FIG. 13 is a k-ω plot of data processed from an array of pressure sensors use to measure the speed of sound of a coal/air mixture flowing in a pipe, in accordance with the present invention.

FIG. 13 shows a k-ω plot generated for acoustic sound field of a coal/air mixture flowing through a pipe. Two acoustic ridges are clearly evident. Each of the slopes of the two depicted acoustic ridges respectively defines the speed of sound traveling with and against the mean flow.

The sonar flow meter 10 of FIG. 1 is configured and programmed to measure and utilize the speed of sound propagating through a particle/fluid mixture 12 flowing in a pipe 14 to determine volumetric flow rate. Referring to FIG. 14, a flow meter 70 embodying the present invention includes the ability to measure volumetric flow rate of the mixture by measuring the unsteady pressures generated by vortical disturbance 88 propagating in the mixture. The flow meter 70 uses one or both of the following techniques to determine the convection velocity of the vortical disturbances within the fluid/particle mixture 12 by:

1) Cross correlating unsteady pressure variations using an array of unsteady pressure sensors.
2) Characterizing the convective ridge of the vortical disturbances using an array of unsteady pressure sensors.

The overwhelming majority of industrial process flows involve turbulent flow. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar flow metering technology, understanding the time-averaged velocity profile in turbulent flow provides a means to interpret the relationship between speed at which coherent structures convect and the volumetrically averaged flow rate within a pipe.

Figure 15:
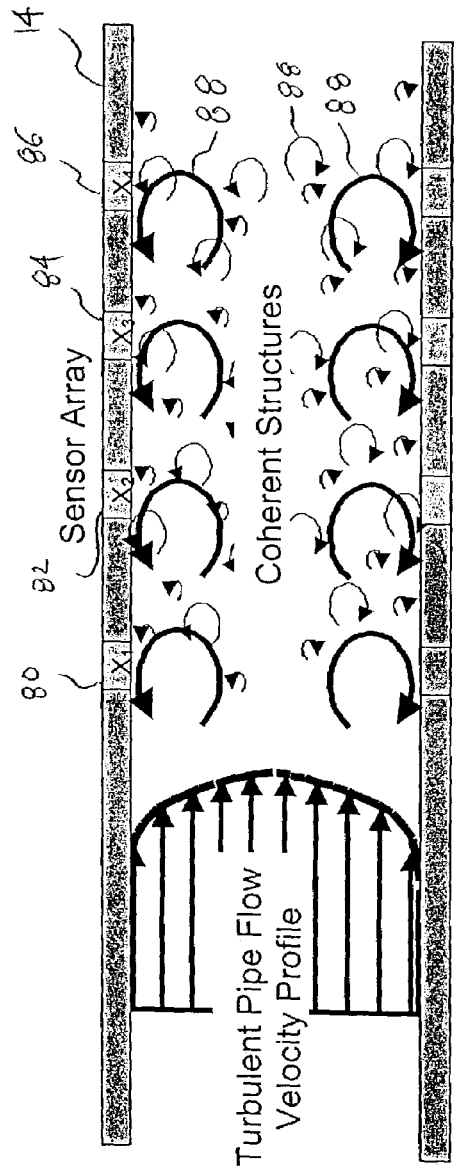
FIG. 15 is a cross-sectional view of a pipe showing a turbulent pipe flow velocity profile.

For turbulent flows, the time-averaged axial velocity varies with radial position, from zero at the wall to a maximum at the centerline of the pipe. The flow near the wall is characterized by steep velocity gradients and transitions to relatively uniform core flow near the center of the pipe. FIG. 15 shows a representative schematic of a velocity profile and coherent vortical flow structures 88 present in fully developed turbulent pipe flow 12. The vortical structures 88 are superimposed over time averaged velocity profile within the pipe 14 and contain temporally and spatially random fluctuations with magnitudes typically less than 10% percent of the mean flow velocity.

From a volumetric flow measurement perspective, the volumetrically averaged flow velocity is of interest. The volumetrically averaged flow velocity, defined as $V=Q/A$, is a useful, but arbitrarily defined property of the flow. Here, A is the cross sectional area of the pipe and Q is the volumetric flow rate. In fact, given the velocity profile within the pipe, little flow is actually moving at this speed.

Turbulent pipes flows are highly complex flows. Predicting the details of any turbulent flow is one of nature's great-unsolved problems. However, much is known regarding the statistical properties of the flow. For instance, turbulent pipe flows contain self-generating, coherent vortical structures often termed "turbulent eddies". The maximum length scale of these eddies is set by the diameter of the pipe. These structures remain coherent for several pipe diameters downstream, eventually breaking down into progressively smaller eddies until the energy is dissipated by viscous effects.

Experimental investigations have established that eddies generated within turbulent boundary layers convect at roughly 80% of maximum flow velocity. For pipe flows, this implies that turbulent eddies will convect at approximately the volumetrically averaged flow velocity within the pipe. The precise relationship between the convection speed of turbulent eddies and the flow rate for each class of meters can be calibrated empirically as described below.

The flow meter 70 of FIG. 14 determines the convection velocity of the vortical disturbances within the fluid/particle mixture by cross correlating unsteady pressure variations using an array of unsteady pressure sensors, similar to that shown in U.S. patent application Ser. No. 10/007,736, filed Nov. 8, 2001, entitled "Flow Rate Measurement Using Unsteady Pressures", which is incorporated herein by reference.

Referring to FIG. 14, the flow meter 70 includes a sensing section 72 along a pipe 12 and a signal processing unit 74. The pipe (or conduit) 14 has two measurement regions 76,78 located a distance $\Delta X$ apart along the pipe 14. At the first measurement region 76 are two unsteady (or dynamic or ac) pressure sensors 80,82, located a distance $X_1$ apart, capable of measuring the unsteady pressure in the pipe 14, and at the second measurement region 78, are two other unsteady pressure sensors 84,86, located a distance $X_2$ apart, capable of measuring the unsteady pressure in the pipe 14. Each pair of pressure sensors 80,82 and 84,86 act as spatial filters to remove certain acoustic signals from the unsteady pressure signals, and the distances $X_1,X_2$ are determined by the desired filtering characteristic for each spatial filter, as discussed hereinafter.

The flow meter 70 of the present invention measures velocities associated with unsteady flow fields and/or pressure disturbances represented by 88 associated therewith relating to turbulent eddies (or vortical flow fields), inhomogeneities in the flow (such as bubbles, slugs, and the like), or any other properties of the flow, fluid, or pressure, having time varying or stochastic properties that are manifested at least in part in the form of unsteady pressures. The vortical flow fields are generated within the fluid of the pipe 14 by a variety of non-discrete sources such as remote machinery, pumps, valves, elbows, as well as the fluid flow itself. It is this last source, the fluid flowing within the pipe, that is a generic source of vortical flow fields primarily caused by the shear forces between the fluid and the wall of the pipe that assures a minimum level of disturbances for any fluid piping systems for which the present invention takes unique advantage. The flow generated vortical flow fields generally increase with mean flow velocity and do not occur at any predeterminable frequency. As such, no external discrete vortex generating source is required within the present invention and thus may operate using passive detection. It is within the scope of the present that the pressure sensor spacing may be known or arbitrary and that as few as two sensors are required if certain information is known about the acoustic properties of the system as will be more fully described herein below.

The vortical flow fields 88 are, in general, comprised of pressure disturbances having a wide variation in length scales and which have a variety of coherence length scales such as that described in the reference "Sound and Sources of Sound", A. P. Dowling et al, Halsted Press, 1983, which is incorporated by reference to the extend of understanding the invention. Certain of these vortical flow fields 88 convect at or near/or related to the mean velocity of at least one of the elements within a mixture flowing in a pipe. The vortical pressure disturbances 15 that contain information regarding convection velocity have temporal and spatial length scales as well as coherence length scales that differ from other disturbances in the flow. The present invention utilizes these properties to preferentially select disturbances of a desired axial length scale and coherence length scale as will be more fully described hereinafter. For illustrative purposes, the terms vortical flow field and vortical pressure field will be used to describe the above-described group of unsteady pressure fields having temporal and spatial length and coherence scales described herein.

The pressures $P_1,P_2,P_3,P_4$ may be measured through holes in the pipe 14 ported to external pressure sensors or by other techniques discussed hereinafter. The pressure sensors 80,82,84,86 provide time-based pressure signals $P_1(t),P_2(t),P_3(t),P_4(t)$ on lines 90-93, respectively, to signal processing unit 74 which provides a convection velocity signal $U_c(t)$ on a line 96 which is related to an average flow rate $U_f(t)$ of the fluid flowing in the pipe 14.

Also, some or all of the functions within the signal processing unit 74 may be implemented in software (using a microprocessor or computer) and/or firmware, or may be implemented using analog and/or digital hardware, having sufficient memory, interfaces, and capacity to perform the functions described herein.

In particular, in the processing unit 74, the pressure signal $P_1(t)$ on the line 90 is provided to a positive input of a summer 100 and the pressure signal $P_2(t)$ on the line 91 is provided to a negative input of the summer 100. The output of the summer 100 is provided to line 104 indicative of the difference between the two pressure signals $P_1,P_2$ (e.g., $P_1-P_2=P_{as1}$).

The pressure sensors 80,82 together with the summer 100 create a spatial filter 76. The line 104 is fed to bandpass filter 108, which passes a predetermined passband of frequencies and attenuates frequencies outside the passband. In accordance with the present invention, the passband of the filter 108 is set to filter out (or attenuate) the dc portion and the high frequency portion of the input signals and to pass the frequencies therebetween. Other passbands may be used in other embodiments, if desired. Passband filter 108 provides a filtered signal $P_{asf1}$ on a line 112 to Cross-Correlation Logic 116, described hereinafter.

The pressure signal $P_3(t)$ on the line 92 is provided to a positive input of a summer 102 and the pressure signal $P_4(t)$ on the line 93 is provided to a negative input of the summer 102. The pressure sensors 83,84 together with the summer 102 create a spatial filter 78. The output of the summer 102 is provided on a line 106 indicative of the difference between the two pressure signals $P_3,P_4$ (e.g., $P_3-P_4=P_{as2}$). The line 106 is fed to a bandpass filter 110, similar to the bandpass filter 108 discussed hereinbefore frequencies within the passband and attenuates frequencies outside the passband. The filter 110 provides a filtered signal $P_{asf2}$ on a line 114 to the Cross-Correlation Logic 116. The signs on the summers 100,102 may be swapped if desired, provided the signs of both summers are swapped together. In addition, the pressure signals $P_1,P_2,P_3,P_4$ may be scaled prior to presentation to the summers 100,102.

The Cross-Correlation Logic 116 calculates a known time domain cross-correlation between the signals $P_{asf1}$ and $P_{asf2}$ on the lines 112,114, respectively, and provides an output signal on a line 118 indicative of the time delay $\tau$ it takes for an vortical flow field 88 (or vortex, stochastic, or vortical structure, field, disturbance or perturbation within the flow) to propagate from one sensing region 76 to the other sensing region 78. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field 88 also has a stochastic or vortical pressure disturbance associated with it. In general, the vortical flow disturbances 88 are distributed throughout the flow, particularly in high shear regions, such as boundary layers (e.g., along the inner wall of the pipe 14) and are shown herein as discrete vortical flow fields 88. Because the vortical flow fields (and the associated pressure disturbance) convect at or near the mean flow velocity, the propagation time delay $\tau$ is related to the velocity of the flow by the distance $\Delta X$ between the measurement regions 76,78, as discussed hereinafter.

Although pressure disturbances associated with vortical flow fields 88 occur naturally in most flow conditions, an optional circumferential groove (not shown) may be used in the inner diameter of the pipe 14 to help generate unsteady flow fields in the form of vertices into the flow. However, the groove is not required for the present invention to operate, due to vortex generation which naturally occurs along the pipe inner wall, as discussed hereinbefore. Instead of a single circumferential groove a plurality of axially spaced circumferential grooves may be used. The dimensions and geometry of the groove(s) 70 may be set based on the expected flow conditions and other factors. Other techniques may be used as vortex generators if desired including those that may protrude within the inner diameter of pipe 14.

Referring to FIG. 14, a spacing signal $\Delta X$ on a line 120 indicative of the distance $\Delta X$ between the sensing regions 76,78 is divided by the time delay signal $\tau$ on the line 118 by a divider 122 which provides an output signal on the line 96 indicative of the convection velocity $U_c(t)$ of the fluid flowing in the pipe 14, which is related to (or proportional to or approximately equal to) the average (or mean) flow velocity $U_f(t)$ of the fluid, as defined below:

$$U_c(t)=\Delta X/\tau \propto U_f(t) \qquad \text{Eq. 1}$$

The convection velocity $U_c(t)$ may then be calibrated to more precisely determine the mean velocity $U_f(t)$ if desired. The result of such calibration may require multiplying the value of the convection velocity $U_c(t)$ by a calibration constant (gain) and/or adding a calibration offset to obtain the mean flow velocity $U_f(t)$ with the desired accuracy. Other calibration may be used if desired. For some applications, such calibration may not be required to meet the desired accuracy. The velocities $U_f(t),U_c(t)$ may be converted to volumetric flow rate by multiplying the velocity by the cross-sectional area of the pipe.

Figure 16:
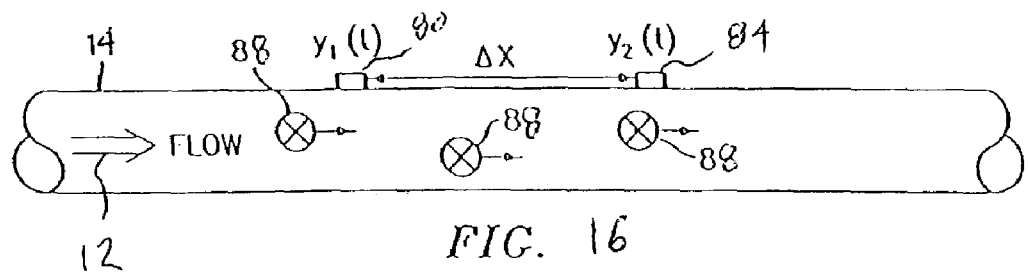
FIG. 16 is a side elevational view of another embodiment of a flow meter for measuring the vortical disturbances in a pipe, in accordance with the present invention.
Figure 17:
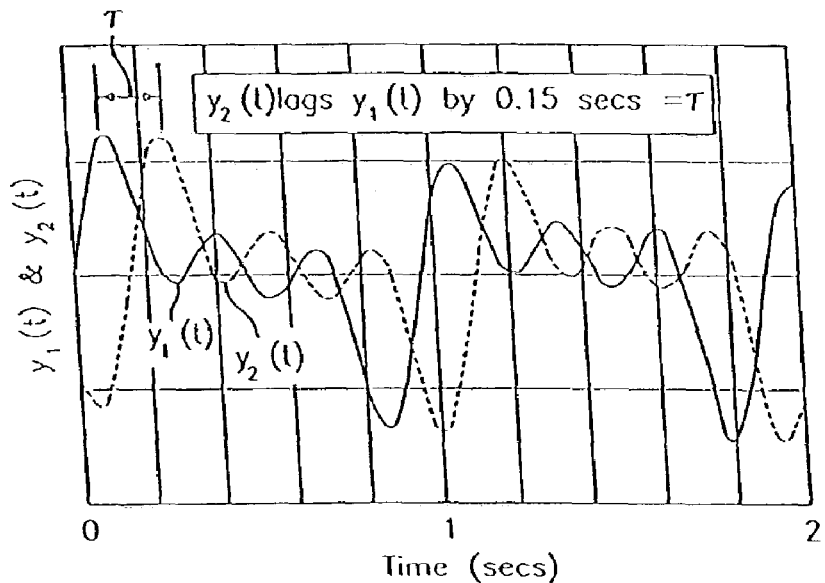
FIG. 17 is a plot of the pressure signals measured by a pair of pressure sensors of the flow meter of FIG. 16.
Figure 18:
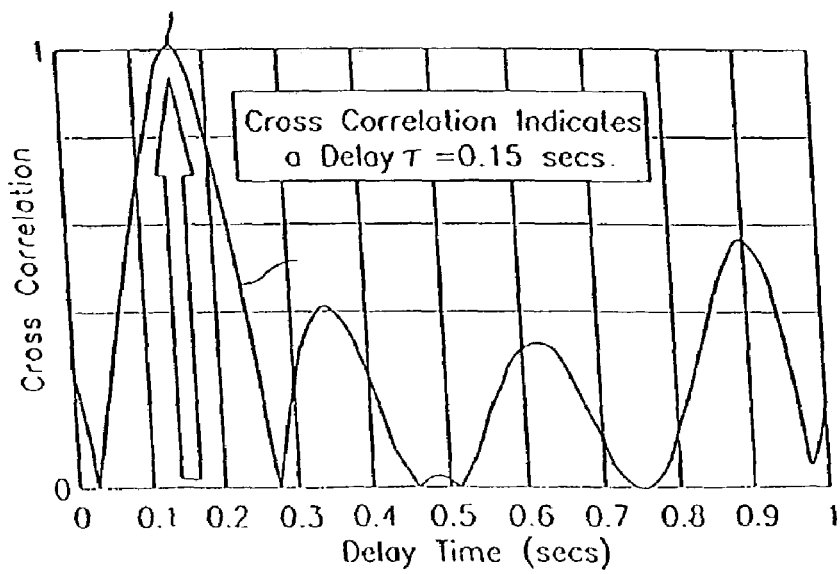
FIG. 18 is a plot of the cross-correlation of the pressure signals plotted in FIG. 17.

Referring to FIGS. 16-18, as is known, cross-correlation may be used to determine the time delay $\tau$ between two signals $y_1(t),y_2(t)$ separated by a known distance $\Delta X$, that are indicative of quantities 80 that convect with the flow (e.g., density perturbations, concentration perturbations, temperature perturbations, vortical pressure disturbances, and other quantities). In FIG. 16, the signal $y_2(t)$ lags behind the signal $y_1(t)$ by 0.15 seconds. If a time domain cross-correlation is taken between the two signals $y_1(t),y_2(t)$, the result is shown in FIG. 17 as a curve 124. The highest peak 126 of the curve 124 shows the best fit for the time lag $\tau$ between the two signals $y_1(t),y_2(t)$ is at 0.15 seconds which matches the reference time delay shown in FIG. 17.

Referring to FIG. 14, as discussed hereinbefore, since pressure disturbances associated within the vortical flow field 88 convect (or flow) at or near the average velocity of the fluid flowing in the pipe 14, the vortical pressure disturbances observed at the downstream location are substantially a time lagged version of the vortical pressure disturbances observed at the upstream location. However, the total vortical pressure perturbations or disturbances in a pipe may be expressed as being comprised of vortical pressure disturbances ($P_{vortical}$), acoustic pressure disturbances ($P_{acoustic}$) and other types of pressure disturbances ($P_{other}$) as shown below expressed in terms of axial position along the pipe at any point in time:

$$P(x,t)=P_{vortical}(x,t)+P_{acoustic}(x,t)+P_{other}(x,t) \qquad \text{Eq. 2}$$

As a result, the unsteady pressure disturbances $P_{vortical}$ can be masked by the acoustic pressure disturbances $P_{acoustic}$ and the other types of pressure disturbances $P_{other}$. In particular, the presence of the acoustic pressure disturbances that propagate both upstream and downstream at the speed of sound in the fluid (sonic velocity), can prohibit the direct measurement of velocity from cross-correlation of direct vortical pressure measurements.

The present invention uses temporal and spatial filtering to precondition the pressure signals to effectively filter out the acoustic pressure disturbances $P_{acoustic}$ and other long wavelength (compared to the sensor spacing) pressure disturbances in the pipe 14 at the two sensing regions 76,78 and retain a substantial portion of the vortical pressure disturbances $P_{vortical}$ associated with the vortical flow field 88 and any other short wavelength (compared to the sensor spacing) low frequency pressure disturbances $P_{other}$. In accordance with the present invention, if the low frequency pressure disturbances $P_{other}$ are small, they will not substantially impair the measurement accuracy of $P_{vortical}$.

The $P_{vortical}$ dominated signals from the two regions 76,78 are then cross-correlated to determine the time delay τ between the two sensing locations 76,78. More specifically, at the sensing region 72, the difference between the two pressure sensors 80,82 creates a spatial filter 76 that effectively filters out (or attenuates) acoustic disturbances for which the wavelength λ of the acoustic waves propagating along the fluid is long (e.g., ten-to-one) compared to the spacing $X_1$ between the sensors. Other wavelength to sensor spacing ratios may be used to characterize the filtering, provided the wavelength to sensor spacing ratio is sufficient to satisfy the two-to-one spatial aliasing Nyquist criteria.

Thus, if the pressure sensors $P_1,P_2$ have an axial spacing $X_1$, and assuming that the spatial filter 76 will attenuate acoustic wavelengths longer than about 10 times the sensor spacing $X_1$, the smallest acoustic wavelength μmin that is attenuated would be:

$$\lambda_{min}=10(X_1) \qquad \text{Eq. 3}$$

One dimensional acoustic disturbances are also governed by the following known inverse wavelength-frequency relation:

$$\lambda=a/f \text{ or } f=a/\lambda \qquad \text{Eq. 4}$$

where a is the speed of sound of the fluid, f is the frequency of the acoustic disturbance, and λ is the wavelength of the acoustic disturbance.

Using Eq. 4, such a spatial filter would filter out frequencies below about:

$$f_{max}=a/\lambda_{min} \qquad \text{Eq. 5}$$

The above discussion on the spatial filter 76 also applies to the second spatial filter 78 comprising the other pair of pressure signals $P_3,P_4$, axially spaced a distance $X_2$ apart, which provides the differenced vortical pressure signal $P_{as2}$.

The second technique of determining the convection velocity of the vortical disturbances within the fluid/particle mixture is by characterisizing the convective ridge of the vortal disturbances using an array of unsteady pressure sensors, as will be described.

The sonar flow metering methodology uses the convection velocity of coherent structure with turbulent pipe flows to determine the volumetric flow rate. The convection velocity of these eddies 88 is determined by applying sonar arraying processing techniques to determine the speed at which the eddies convect past an axial array of unsteady pressure measurements distributed along the pipe 14.

The sonar-based algorithms determine the speed of the eddies by characterizing both the temporal and spatially frequency characteristics of the flow field. For a train of coherent eddies convecting past a fixed array of sensors, the temporal and spatial frequency content of pressure fluctuations are related through the following relationship:

$$\omega = \frac{k}{U_{convect}}$$

Here k is the wave number, defined as $k=2\pi/\lambda$ and has units of 1/length, ω is the temporal frequency in rad/sec, and $U_{convect}$ is the convection velocity. Thus, the shorter the wavelength (larger k) is, the higher the temporal frequency.

In sonar array processing, the spatial/temporal frequency content of time stationary sound fields are often displayed using "k-ω plots". K-ω plots are essentially three-dimensional power spectra in which the power of a sound field is decomposed into bins corresponding to specific spatial wave numbers and temporal frequencies. On a k-ω plot, the power associated with a pressure field convecting with the flow is distributed in regions which satisfies the dispersion relationship developed above. This region is termed "the convective ridge" (Beranek, 1992) and the slope of this ridge on a k-ω plot indicates the convective velocity of the pressure field. This suggests that the convective velocity of turbulent eddies, and hence flow rate within a pipe, can be determined by constructing a k-ω plot from the output of a phased array of sensor and identifying the slope of the convective ridge.

Figure 19:
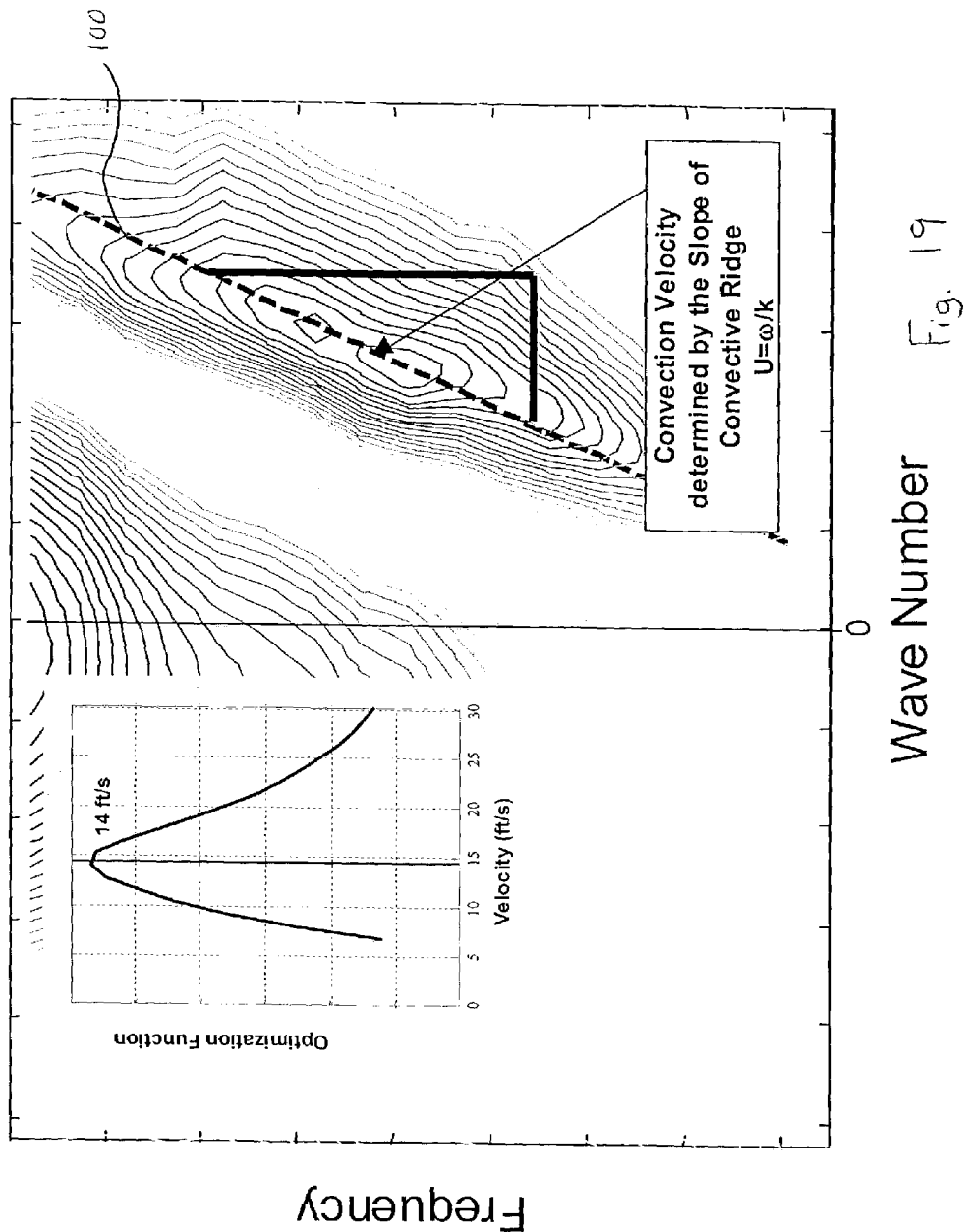
FIG. 19 is a k-ω plot of data processed from a flow meter embodying the present invention that illustrates slope of the convective ridge, and a plot of the optimaztion function of the convective ridge, in accordance with the present invention.

FIG. 19 shows an example of a k-ω plot generated from a phased array of pressure sensors. The power contours show a well-defined convective ridge. A parametric optimization method was used to determine the "best" line representing the slope of the convective ridge 100. For this case, a slope of 14.2 ft/sec was determined. The intermediate result of the optimization procedure is displayed in the insert, showing that optimized value is a unique and well-defined optima.

The k-ω plot shown in FIG. 19 illustrates the fundamental principle behind sonar based flow measure, namely that axial arrays of pressure sensors can be used in conjunction with sonar processing techniques to determine the speed at which naturally occurring turbulent eddies convect within a pipe.

The pressure sensors 15-18 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 15-18 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702. Alternatively, the sensors 14 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 14 if desired.

It is also within the scope of the present invention that any other strain sensing technique may be used to measure the variations in strain in the pipe, such as highly sensitive piezoelectric, electronic or electric, strain gages attached to or embedded in the pipe 14.

In certain embodiments of the present invention, a piezoelectronic pressure transducer may be used as one or more of the pressure sensors 15-18 and it may measure the unsteady (or dynamic or ac) pressure variations inside the pipe 14 by measuring the pressure levels inside of the pipe. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Figure 20:
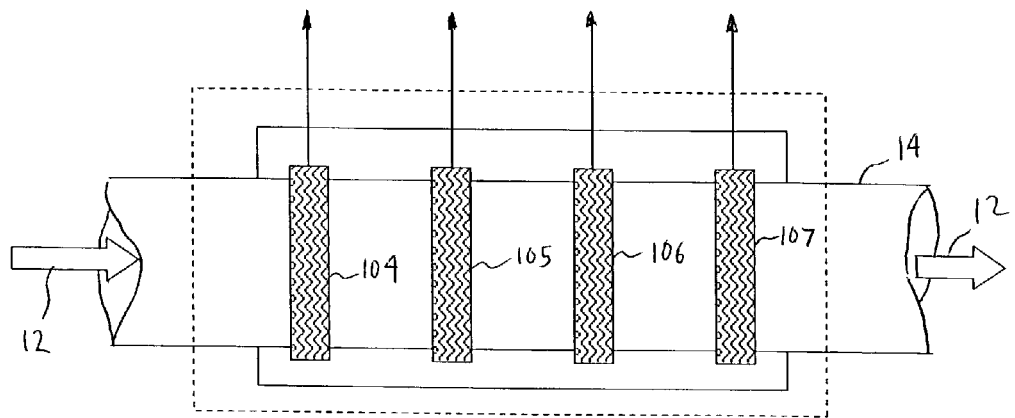
FIG. 20 is a side elevational view of a plurality of pressure sensors, having PVDF, clamped to the outer surface of the pipe, in accordance with the present invention.

Furthermore the present invention contemplates that each of the pressure sensors 15-18 of the flow meters 10,70 may include a piezoelectric sensor 104-107 that provides a piezoelectric material 110 to measure the unsteady pressures of the fluid/particle mixture 12 as shown in FIG. 20. The piezoelectric material, such as the polymer, polarized fluoropolymer, polyvinylidene fluoride (PVDF), measures the strain induced within the process pipe 14 due to unsteady pressure variations within the process mixture 12. Strain within the pipe is transduced to an output voltage or current by the attached piezoelectric sensors 104-107.

Figure 21:
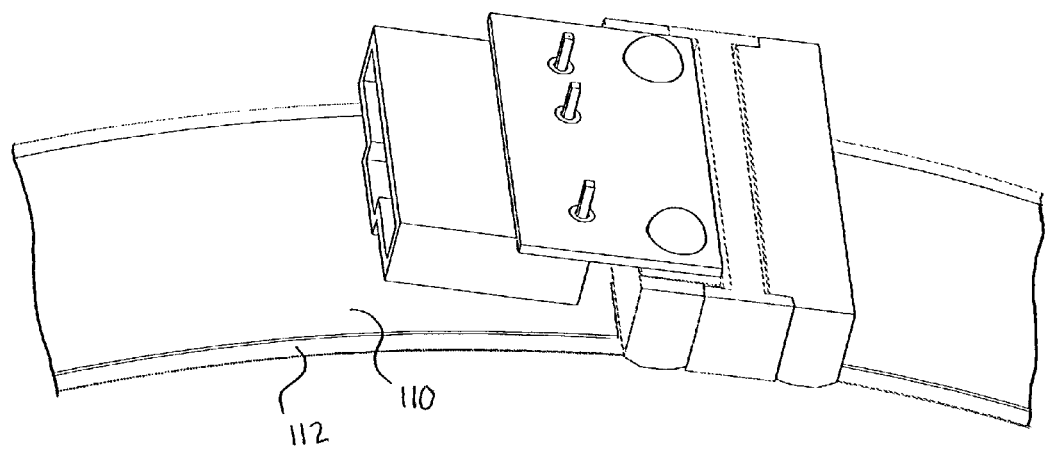
FIG. 21 is a partial perspective view of one of the pressure sensors of FIG. 20.

As best shown in FIG. 21, the PVDF material 110 is adhered to the outer surface of a steel strap 112 that extends around and clamps onto the outer surface of the pipe 14. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc., which is incorporated herein by reference. The advantages of this technique are the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals.
5. Higher Temperatures (140 C) (co-polymers)

While the present invention is capable of measuring solid particles suspended in a fluid, one will appreciate that other multi-phase mixtures or flows may be measured using an array of sensors, such as steam flow. It is further recognize the effects of dispersion on large solid particles in a fluid would be similar to large droplets of a liquid dispersed in a gas or air, and thus similar considerations when measuring the steam quality and droplet size should be addressed.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a dispersive particle/fluid mixture flowing in a pipe, said apparatus comprising:
    an array of at least two sensors, disposed at different axial locations along the pipe, to measure a pressure within the pipe at each corresponding axial location, each of said sensors providing a pressure signal indicative of the pressure within the pipe at said corresponding axial location; and
    a signal processor, responsive to said pressure signals, to determine the speed of sound propagating through the dispersive mixture as a function of frequency which includes a frequency in the transitional frequency range and to use the speed of sound and a dispersion model of the dispersive mixture to provide a signal indicative of the at least one parameter of the dispersive mixture in the pipe.

2. The apparatus of claim 1 wherein said signal processor comprises logic which calculates a speed at which sound propagates along said array.

3. The apparatus of claim 2 wherein said pressure signals each comprise a frequency based signal and wherein said signal processor comprises logic which calculates a ratio of two of said frequency based signals.

4. The apparatus of claim 1 wherein the dispersion model is numerically derived.

5. The apparatus of claim 4 wherein the numerically derived dispersion model is:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

wherein $a_{mix}(\omega)$=speed of sound propagating through the mixture; $a_f$=speed of sound propagating through the fluid; $\varphi_p$=volume fraction of the particles; $\omega$=frequency; $\rho_p, \rho_f$=density of particles and fluid, respectively; $v$=volume of a particle; $K$=proportionality constant.

6. The apparatus of claim 1 wherein each sensor measures an acoustic pressure and provides a signal indicative of an acoustic noise within the pipe.

7. The apparatus of claim 1 wherein said signal processor comprises logic which calculates a frequency based signal for each of said pressure signals.

8. The apparatus of claim 1 wherein the array of sensors comprises at least one of 3, 4, 5, 6, 7, 8, 9, 10, 11, 12, 13, 14, 15 and 16 sensors disposed at respective axial locations.

9. The apparatus of claim 1 wherein the signal processor comprises logic which calculates a fluid composition of the dispersive mixture in the pipe.

10. The apparatus of claim 1 wherein at least one of said sensors measures strain on the pipe.

11. The apparatus of claim 1 wherein the array of sensors are spaced sufficiently such that the entire length of the array is at least a significant fraction of the measured wavelength of the acoustic waves being measured.

12. The apparatus of claim 1 wherein the signal processor uses the speed of sound propagating through the dispersive mixture to characterize dispersion properties of the dispersive mixture and compares the dispersion properties of the dispersive mixture to a dispersion model of the dispersive mixture to provide a signal indicative of the at least one parameter of the dispersive mixture.

13. The apparatus of claim 1 wherein the dispersion model is empirically derived.

14. The apparatus of claim 1 wherein the at least one parameter of the dispersive mixture includes at least one of a particle/fluid composition, the volumetric phase fraction, the volumetric flow rate, the size of the particles, the mass flow, density, the velocity of the dispersive mixture in the pipe, and the speed of sound propagating through the dispersive mixture in the pipe.

15. The apparatus of claim 1 wherein the signal processor further characterizes the dispersion properties of the dispersive mixture in response to at least one of the pressure of the dispersive mixture, temperature of the dispersive mixture, density of particle phase and density of the fluid phase.

16. The apparatus of claim 1 wherein the signal processor compares at least the transitional frequency range of the dispersion model to determine the average size of the particles in the dispersive mixture.

17. The apparatus of claim 1 wherein the signal processor compares at least one of the lower frequency range and the transitional frequency range of the dispersion model to determine the particle/fluid ratio of the dispersive mixture.

18. The apparatus of claim 1 wherein the signal processor defines an acoustic ridge in the k-ω plane and determines the slope of the at least a portion of an acoustic ridge to determine the speed of sound propagating through the dispersive mixture.

19. The apparatus of claim 1 wherein the sensors include at least one of pressure sensors and strain-based sensors.

20. A method for measuring at least one parameter of a dispersive particle/fluid mixture flowing in a pipe, said method comprising:
    measuring pressures within the pipe at at least two axial measurement locations along the pipe to provide a pressure signal indicative of the pressure within the pipe at each of the at least two axial measurement locations; and
    calculating the at least one parameter of the dispersive mixture in the pipe using the pressure measured at the axial measurement locations to determine the speed of sound propagating through the dispersive mixture as a function of frequency which includes a frequency in the transitional frequency range and using the speed of sound and a dispersion model of the dispersive mixture.

21. The method of claim 20 wherein the measured pressures are acoustic pressures to provide a signal indicative of an acoustic noise within the pipe.

22. The method of claim 21, wherein the calculating the at least one parameter uses an acoustic pressure to calculate a speed of sound propagating in the pipe.

23. The method of claim 20 wherein the dispersion model is numerically derived.

24. The method of claim 23 wherein the numerically derived dispersion model is:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

wherein $a_{mix}(\omega)$=speed of sound propagating through the mixture; $a_f$=speed of sound propagating through the fluid; $\phi_p$=volume fraction of the particles; $\omega$=frequency; $\rho_p,\rho_f$=density of particles and fluid, respectively; $v$=volume of a particle; K=proportionality constant.

25. The method of claim 20 wherein said calculating the at least one parameter uses the speed of sound propagating through the dispersive mixture to characterize dispersion properties of the dispersive mixture and compares the dispersion properties of the dispersive mixture to a dispersion model of the dispersive mixture to provide a signal indicative of the at least one parameter of the dispersive mixture.

26. The method of claim 20 wherein the dispersion model is empirically derived.

27. The method of claim 20 wherein the at least one parameter of the dispersive mixture includes at least one of a particle/fluid composition, the volumetric phase fraction, the volumetric flow rate, the size of the particles, the mass flow, density, the velocity of the dispersive mixture in the pipe, and the speed of sound propagating through the dispersive mixture in the pipe.

28. The method of claim 20 wherein said calculating the at least one parameter further characterizes the dispersion properties of the dispersive mixture in response to at least one of the pressure of the dispersive mixture, temperature of the dispersive mixture, density of particle phase and density of the fluid phase.

29. The method of claim 20 wherein said calculating the at least one parameter compares at least the intermediate frequency range of the dispersion model to determine the average size of the particles in the dispersive mixture.

30. The method of claim 20 wherein said calculating the at least one parameter compares at least one of the lower frequency range and the intermediate frequency range of the dispersion model to determine the particle/fluid ratio of the dispersive mixture.

31. The method of claim 20 further includes determining a frequency based signal for each of said pressure signals.

32. The method of claim 20 wherein the measuring pressures with the pipe at at least one of 3, 4, 5, 6, 7, 8, 9, 10, 11, 12, 13, 14, 15 and 16 sensors disposed at respective axial locations.

33. The method of claim 20 wherein said calculating the at least one parameter defines an acoustic ridge in the k-$\omega$ plane and determines the slope of the at least a portion of an acoustic ridge to determine the speed of sound propagating through the dispersive mixture.

34. An apparatus for measuring at least one parameter of a dispersive particle/fluid mixture flowing in a pipe, said apparatus comprising:
a signal processor, responsive to a signal indicative of the speed of sound propagating through the dispersive mixture within the pipe as a function of frequency which includes a frequency in the transitional frequency range, to determine the at least one parameter of the dispersive mixture in the pipe using a dispersion model of the dispersive mixture.

35. The apparatus of claim 34 wherein the signal processor receives at least one signal indicative of the speed of sound propagating through the dispersive mixture and determining the speed of sound as a function of frequency in response to the at least one signal.

36. The apparatus of claim 35 further including a least one sensor to provide the at least one signal indicative of the speed of sound propagating through the pipe.

37. The apparatus of claim 34 wherein the signal processor further characterizes the dispersion properties of the dispersive mixture and compares the dispersion properties of the dispersive mixture to a dispersion model of the dispersive mixture to provide a signal indicative of the at least one parameter of the dispersive mixture.

38. The apparatus of claim 34 further includes a meter to measure the speed of sound propagating though the fluid within the pipe.

39. The apparatus of claim 34 wherein the signal processor compares at least the transitional frequency range of the dispersion model to determine the average size of the particles in the dispersive mixture.

40. The apparatus of claim 34 wherein the signal processor compares at least one of the lower frequency range and the transitional frequency range of the dispersion model to determine the particle/fluid ratio of the dispersive mixture.

41. A method for measuring at least one parameter of a dispersive particle/fluid mixture flowing in a pipe; said method comprising:
receiving a signal indicative of the speed of sound propagating through the dispersive mixture as a function of frequency which includes a frequency in the transitional frequency range; and
determining the at least one parameter of the dispersive mixture in the pipe using the signal indicative of the speed of sound and a dispersion model of the dispersive mixture.

42. The method of claim 41 wherein said determining the at least one parameter further characterizes dispersion properties of the dispersive mixture using the signal indicative of the speed of sound propagating through the dispersive mixture and compares the dispersion properties of the dispersive mixture to a dispersion model of the dispersive mixture to provide a signal indicative of the at least one parameter of the dispersive mixture.

43. The method of claim 41 further including determining the speed of sound as a function of frequency in response to at least one signal indicative of the speed of sound propagating through the dispersive mixture.

44. The method of claim 41 further including measuring the speed of sound propagating through the dispersive mixture within the pipe.

45. The method of claim 41 further includes comparing at least the transitional frequency range of the dispersion model to determine the average size of the particles in the dispersive mixture.

46. The method of claim 41 further includes comparing at least one of the lower frequency range and the transitional frequency range of the dispersion model to determine the particle/fluid ratio of the dispersive mixture.

* * * * *